United States Patent
Ishiguro et al.

(10) Patent No.: US 8,282,543 B2
(45) Date of Patent: Oct. 9, 2012

(54) SURGICAL INSTRUMENT AND ENDOSCOPE SURGICAL SYSTEM HAVING SURGICAL INSTRUMENT

(75) Inventors: Tsutomu Ishiguro, Hino (JP); Toshio Nakamura, Hachioji (JP); Jun Hasegawa, Hino (JP)

(73) Assignee: Olympus Medical Systems Corp. (JP)

( * ) Notice: Subject to any disclaimer, the term of this patent is extended or adjusted under 35 U.S.C. 154(b) by 420 days.

(21) Appl. No.: 12/573,201

(22) Filed: Oct. 5, 2009

(65) Prior Publication Data

US 2010/0022837 A1    Jan. 28, 2010

Related U.S. Application Data

(63) Continuation of application No. PCT/JP2007/074714, filed on Dec. 21, 2007.

(30) Foreign Application Priority Data

Apr. 20, 2007  (JP) ................................. 2007-112131

(51) Int. Cl.
*A61B 1/00*   (2006.01)

(52) U.S. Cl. ........ 600/104; 600/106; 600/107; 600/142; 600/146

(58) Field of Classification Search ................... 600/104; 606/32–52
See application file for complete search history.

(56) References Cited

U.S. PATENT DOCUMENTS

| | | | |
|---|---|---|---|
| 4,770,185 A | | 9/1988 | Silverstein et al. |
| 4,922,651 A | * | 5/1990 | Atkinson et al. ............... 47/1.41 |
| 5,624,380 A | * | 4/1997 | Takayama et al. ............ 600/146 |
| 5,843,091 A | | 12/1998 | Holsinger et al. |
| 7,749,156 B2 | * | 7/2010 | Ouchi ........................... 600/104 |
| 7,976,559 B2 | * | 7/2011 | Goldfarb et al. .............. 606/190 |
| 2002/0120260 A1 | | 8/2002 | Morris et al. |
| 2003/0225332 A1 | * | 12/2003 | Okada et al. .................. 600/439 |
| 2005/0096502 A1 | * | 5/2005 | Khalili .......................... 600/106 |

FOREIGN PATENT DOCUMENTS

| | | |
|---|---|---|
| EP | 1 510 178 | 3/2005 |
| JP | 6-114000 | 4/1994 |
| JP | 8-117241 | 5/1996 |
| JP | 2006-223358 | 8/2006 |
| JP | 2007-54400 | 3/2007 |
| WO | WO 2006/108480 A1 | 10/2006 |

OTHER PUBLICATIONS

International Search Report mailed Feb. 26, 2008 in corresponding PCT International Application No. PCT/JP2007/074714.
Office Action issued by the Chinese Patent Office on Aug. 10, 2010 in connection with corresponding Chinese Patent Application No. 200780052671.0.

(Continued)

*Primary Examiner* — Matthew J Kasztejna
(74) *Attorney, Agent, or Firm* — Ostrolenk Faber LLP

(57) ABSTRACT

A surgical instrument having a surgical unit which operates on an operating portion in a body cavity, an accommodation portion capable of accommodating the surgical unit. The surgical instrument having movement manipulation mechanism connected to the surgical unit for moving the surgical unit to a position at which the surgical unit is accommodated in the accommodation portion and to a position at which the surgical unit is exposed from the accommodation portion along the inside of the accommodation portion.

3 Claims, 22 Drawing Sheets

OTHER PUBLICATIONS

English translation of Chinese Office Action issued in connection with Chinese Patent Application No. 200780052671.0 on Aug. 10, 2010.
Notification of Transmittal of Translation of the International Preliminary Report on Patentability dated Nov. 19, 2009, International Preliminary Report on Patentability, and Written Opinion of the International Searching Authority (6 pages total).
Letter from German associate dated May 18, 2011 forwarding the Search Report dated Apr. 21, 2011 to Japanese associate, including discussion of relevancy thereof.
Search Report issued by European Patent Office in connection with corresponding application No. EP 07 85 1066 on Apr. 21, 2011.

* cited by examiner

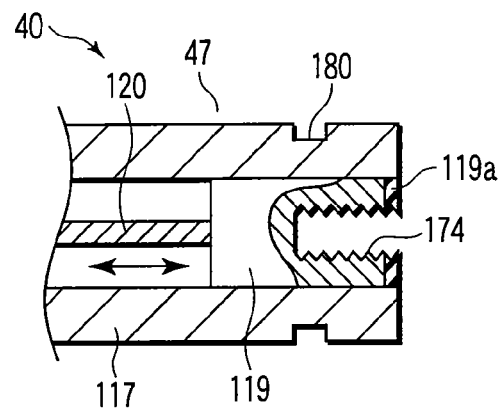
F I G. 7A
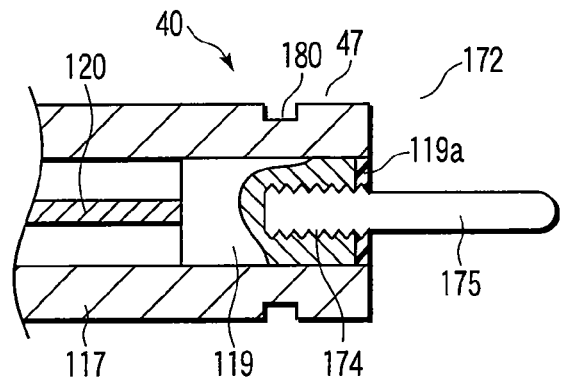
F I G. 7B
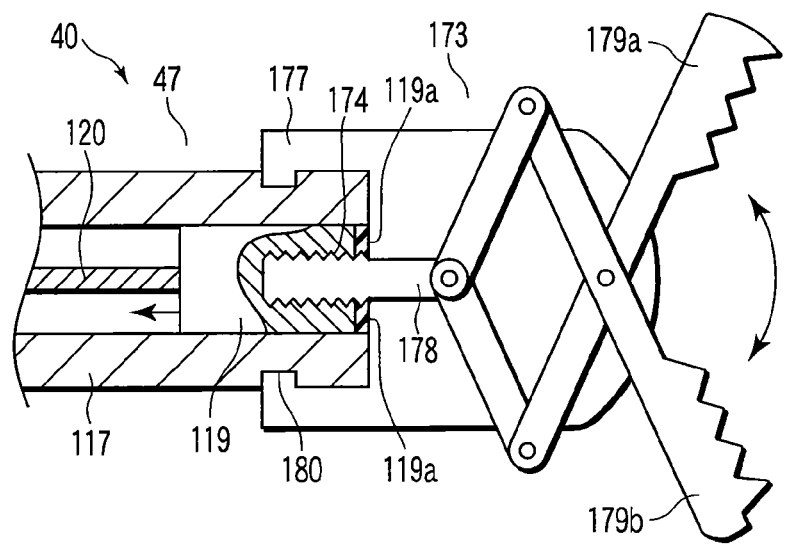
F I G. 7C

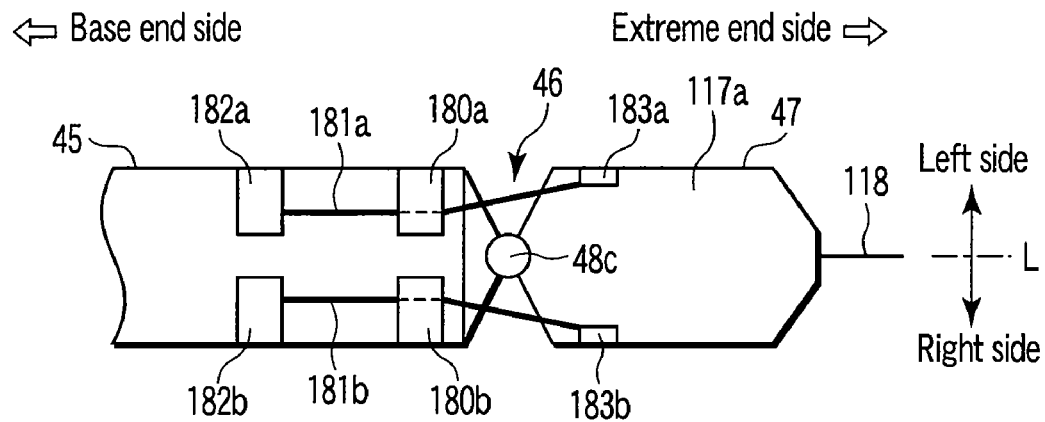
F I G. 8A
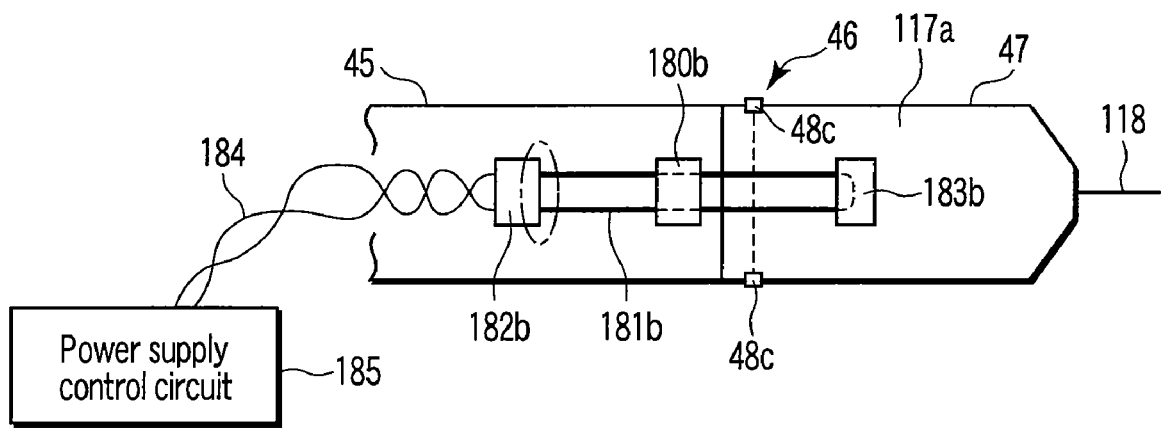
F I G. 8B

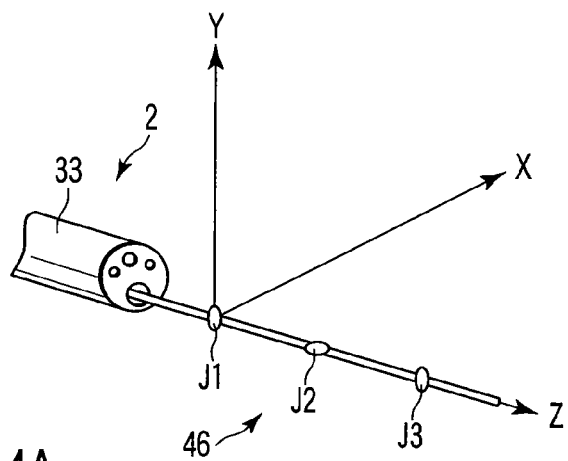
F I G. 14A
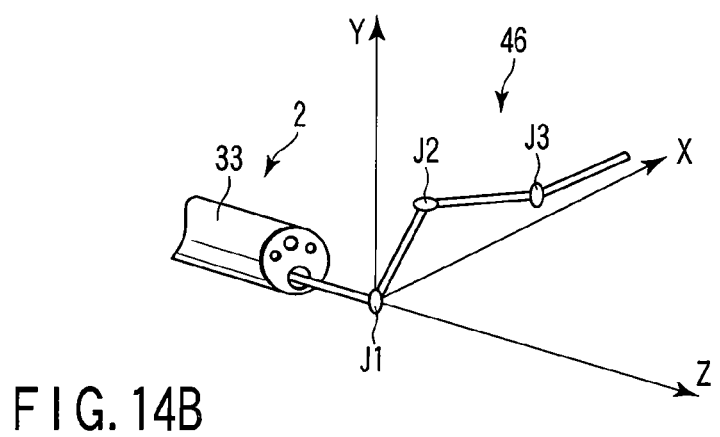
F I G. 14B
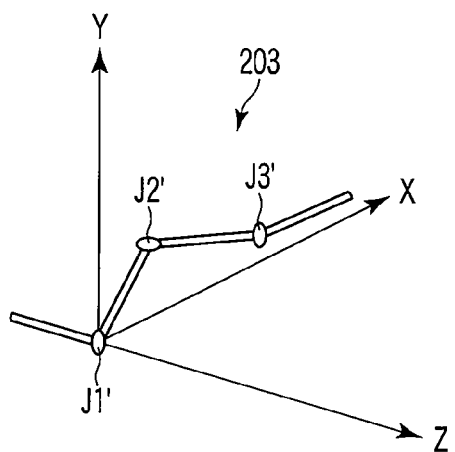
F I G. 15

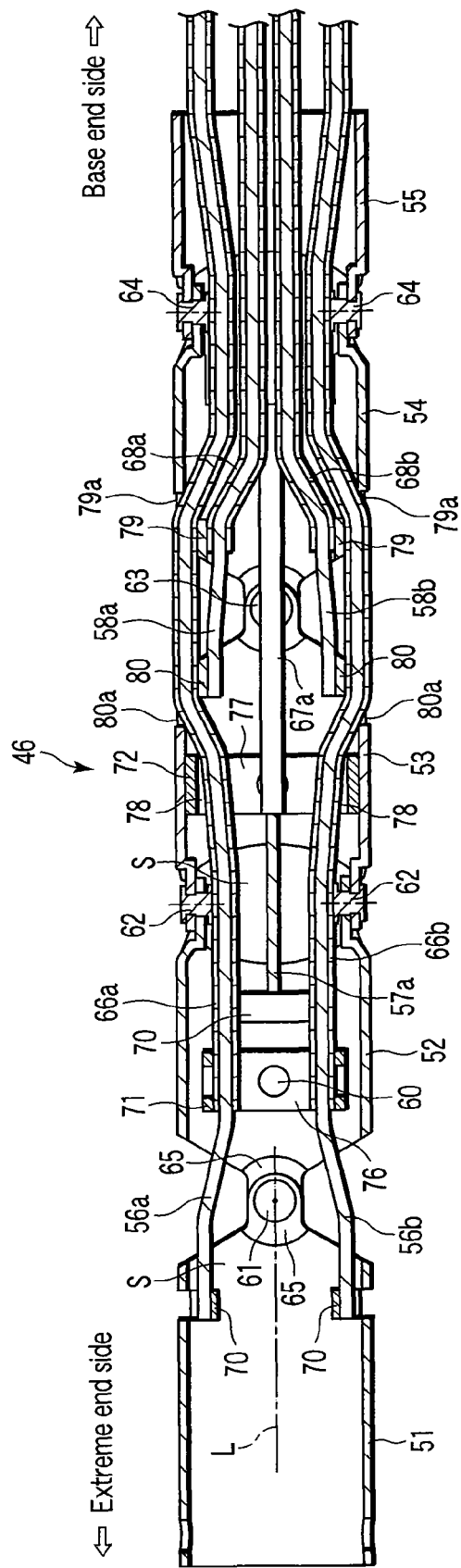
F I G. 18A

Cross section A-A

Cross section B-B

Cross section C-C

Cross section D-D

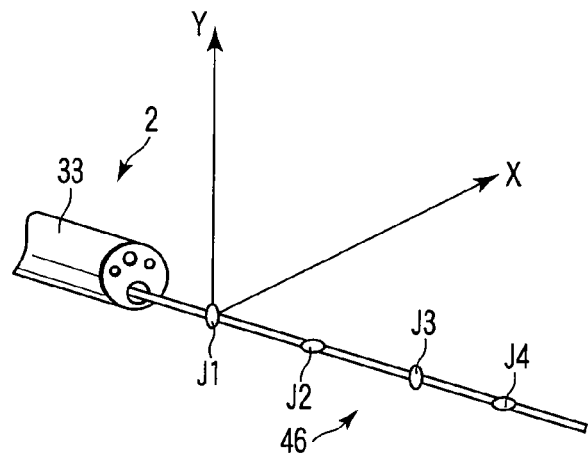
F I G. 20A
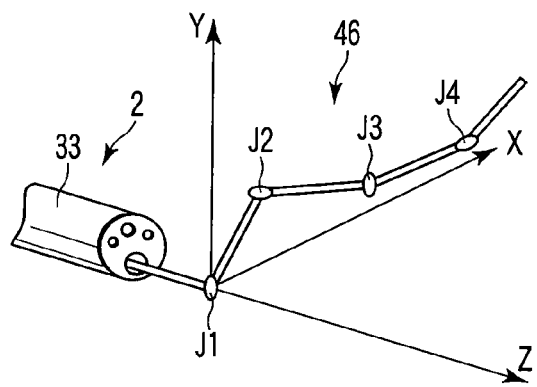
F I G. 20B
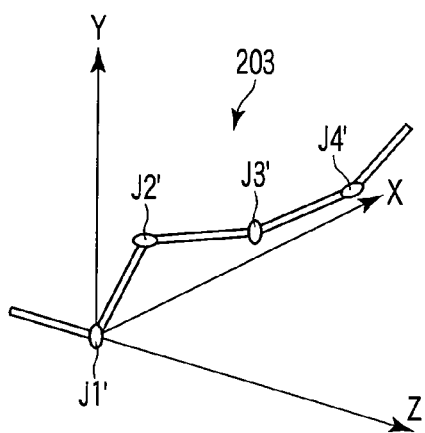
F I G. 21

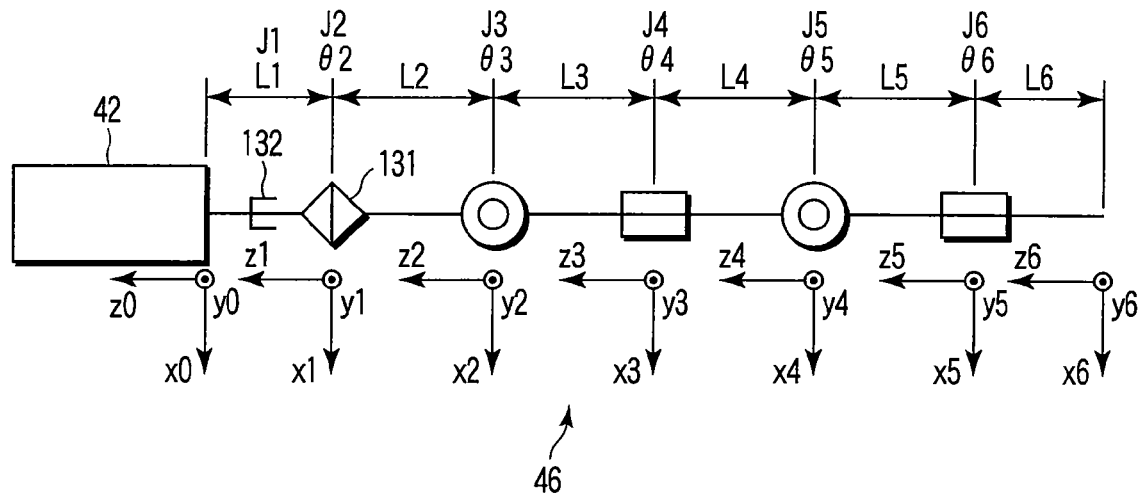
F I G. 22
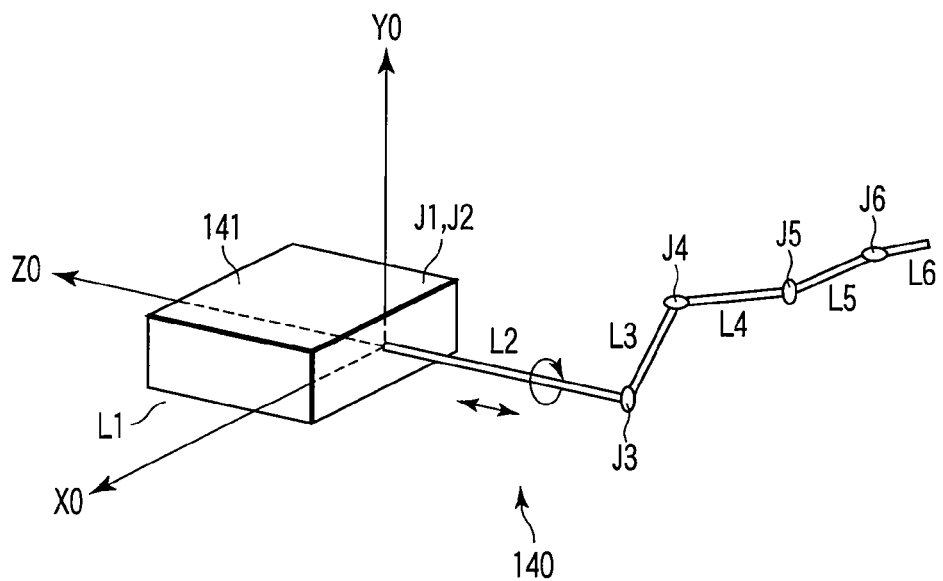
F I G. 23

SURGICAL INSTRUMENT AND ENDOSCOPE SURGICAL SYSTEM HAVING SURGICAL INSTRUMENT

CROSS-REFERENCE TO RELATED APPLICATIONS

This is a Continuation Application of PCT Application No. PCT/JP2007/074714, filed Dec. 21, 2007, which was published under PCT Article 21(2) in Japanese.

This application is based upon and claims the benefit of priority from prior Japanese Patent Application No. 2007-112131, filed Apr. 20, 2007, the entire contents of which are incorporated herein by reference.

BACKGROUND OF THE INVENTION

1. Field of the Invention

The present invention relates to a medical surgical instrument for operating on a portion of a body cavity and an endoscope surgical system having the surgical instrument.

2. Description of the Related Art

Patent Document 1, for example, discloses an endoscope forceps. The endoscope forceps has an insertion portion and a plurality of wire grip portions. Proximal ends of the wire grip portions are fixed to a distal end portion of the insertion portion. The wire grip portions are arranged to bend so that they are expanded (opened) in a radial direction. The wire grip portions pass through an actuator. Forward/backward movement of the actuator opens and closes the wire grip portions. Distal ends of the wire grip portions are formed in a claw-shape. Forward movement of the actuator closes the distal ends of the wire grip portions, and, at this time, they are accommodated in an accommodation portion protruded from a distal end of the actuator.

Patent Document 1: Jpn. Pat. Appln. KOKAI Publication No. 08-117241

BRIEF SUMMARY OF THE INVENTION

Accordingly, the present invention provides a medical surgical instrument and an endoscope surgical system having the surgical instrument in which when the surgical instrument is inserted into an insertion channel of an endoscope and the like, there is no possibility of the surgical instrument scratching the insertion channel and no possibility of the operating energy being applied to the endoscope or a human body by an unintended input manipulation.

An aspect of the present invention provides a surgical instrument comprising an end effector for operating on an operating portion in a body cavity, an accommodation portion capable of accommodating the end effector, and movement manipulation mechanism connected to the end effector for moving the end effector to a position at which the end effector is accommodated in the accommodation portion and to a position at which the end effector is exposed from the accommodation portion along the inside of the accommodation portion.

An aspect of the present invention provides an endoscope surgical system comprising: a surgical instrument, which includes an end effector for operating on an operating portion in a body cavity, an accommodation portion capable of accommodating the end effector, an insertion portion having the end effector and the accommodation portion disposed to a distal end portion, movement manipulation mechanism for moving the end effector to a position at which the end effector is accommodated in the accommodation portion and to a position at which the end effector is exposed from the accommodation portion along the inside of the accommodation portion, and a bending mechanism which is disposed to the insertion portion and moves the distal end portion by being bend; an endoscope having a channel into which the insertion portion is inserted; and manipulation mechanism which is connected to the surgical instrument and manipulates the bending mechanism.

An aspect of the present invention provides an endoscope surgical system comprising: a surgical instrument, which includes an end effector for operating on an operating portion in a body cavity, an accommodation portion capable of accommodating the end effector, an insertion portion having the end effector and the accommodation portion disposed to a distal end, movement manipulation mechanism disposed to a proximal end side of the insertion portion and connected to the end effector to move the end effector to a position at which the end effector is accommodated in the accommodation portion and to a position at which the end effector is exposed from the accommodation portion along the inside of the accommodation portion through a manipulation medium disposed by being inserted into the insertion portion, and a bending mechanism which is disposed to the insertion portion and moves the distal end portion by being bend; an endoscope having a channel into which the insertion portion is inserted; and manipulation mechanism which is connected to the surgical instrument and manipulates the bending mechanism.

BRIEF DESCRIPTION OF THE SEVERAL VIEWS OF THE DRAWING

FIG. 7A is a longitudinal sectional view in the vicinity of a distal end portion according to another embodiment of the present invention.

FIG. 7B is a longitudinal sectional view in the vicinity of a distal end portion according to another embodiment of the present invention.

FIG. 7C is a longitudinal sectional view in the vicinity of a distal end portion according to another embodiment of the present invention.

FIG. 8A is a longitudinal sectional view in the vicinity of a distal end portion according to another embodiment of the present invention.

FIG. 8B is a longitudinal sectional view in the vicinity of a distal end portion according to another embodiment of the present invention.

FIG. 14A is an explanatory view of a multijointed structure in a bending portion of a surgical instrument.

FIG. 14B is an explanatory view of the multijointed structure in the bending portion of the surgical instrument.

FIG. 15 is an explanatory view of a multijointed structure in a joystick.

FIG. 18A is a sectional view of a section of the bending portion which is longitudinally sectioned on a horizontal plane shown by an arrow line A-A of FIG. 17 along a long axis direction of an insertion portion and viewed from above it.

FIG. 20A is an explanatory view of a multijointed structure of a bending portion of a surgical instrument.

FIG. 20B is an explanatory view of the multijointed structure of the bending portion of the surgical instrument.

FIG. 21 is an explanatory view of a multijointed structure of a joystick.

FIG. 22 is an explanatory view of a multijointed structure of a bending portion of a surgical instrument of another embodiment of the present invention.

FIG. 23 is an explanatory view of a multijointed structure of a joystick of the embodiment.

DETAILED DESCRIPTION OF THE INVENTION

Figure 1:
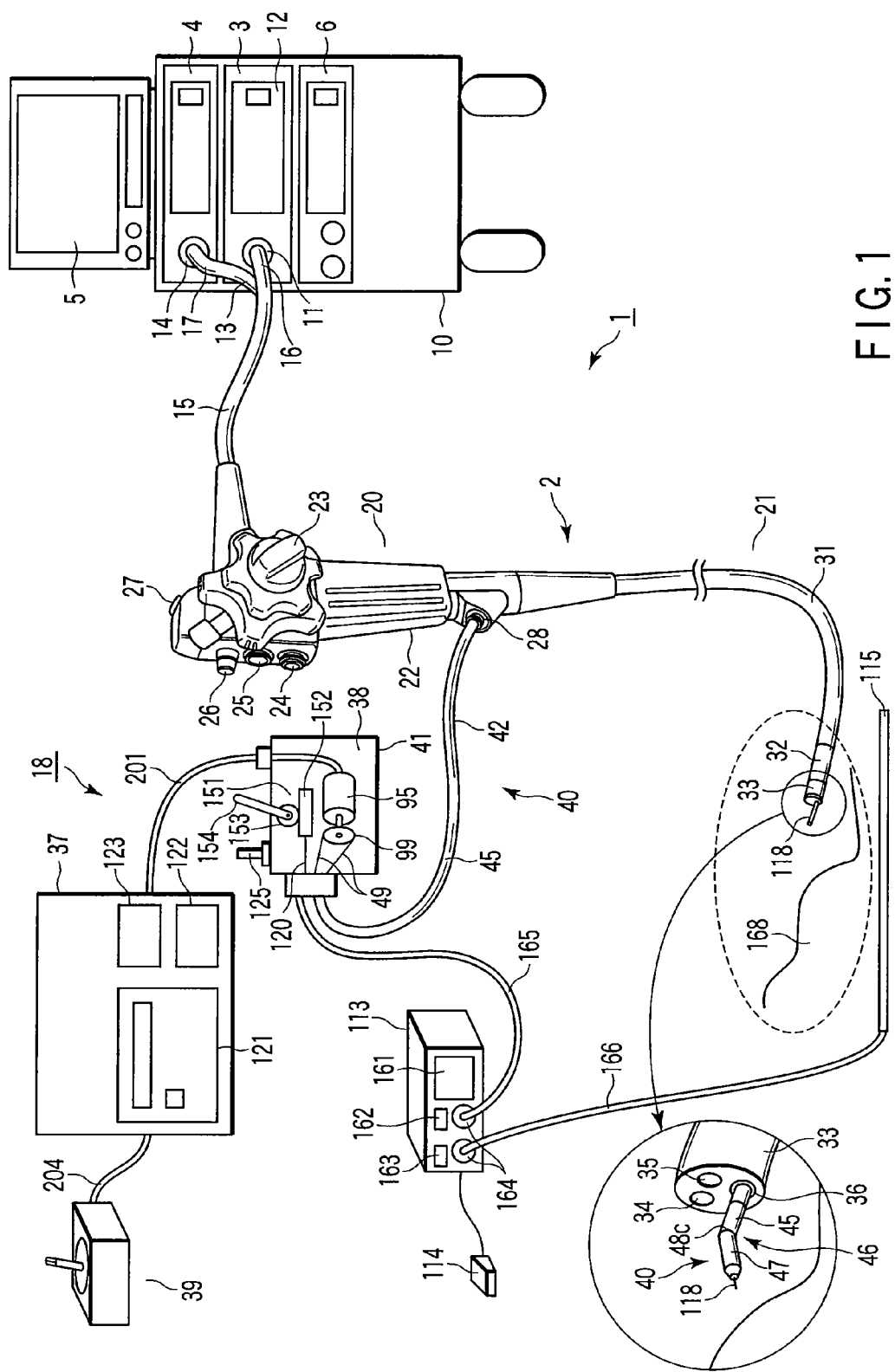
FIG. 1 is a perspective view schematically showing an endoscope apparatus, a surgical instrument, and the like included in an endoscope system according to an embodiment of the present invention.

A surgical instrument (for example, multijointed medical instrument) and an endoscope surgical system having the surgical instrument according to an embodiment of the present invention will be explained below referring to the drawings.

FIG. 1 is a perspective view schematically showing an endoscope apparatus 1, a surgical instrument 40, and the like included in the endoscope system. The endoscope apparatus 1 is composed of an electronic endoscope (endoscope main body) 2 and a peripheral device (device main body) of the endoscope 2.

The peripheral device includes a light source unit 3 for creating endoscope illumination light, an image processing unit 4 for subjecting an image picked up by an image pickup portion (not shown) in the endoscope 2 to various types of image processing, an image display unit (for example, monitor) 5 for displaying an image, image data (an image processed by the image processing unit 4), a state of the device, an instruction of an operator, and the like, a controller 6 for overall control of the endoscope system, and executing an arithmetic operation and the like, an input unit (not shown) having a keyboard and the like, a waste fluid tank (not shown) with a suction pump, a water tank (not shown), and the like. The peripheral device is mounted on a trolley 10.

The light source unit 3 has a connection port 11 connected to a connector unit 16 and a display 12 for displaying an operating state of the light source unit 3 on the front surface thereof.

The image processing unit 4 has a connector receiver 14 connected to a connection cable 13 on a front surface thereof. A connecting unit 17 with a cap is disposed in the proximal end of the connection cable 13. Further, the connector unit 16 is disposed in the distal end of a universal cord 15 of the endoscope 2. An electrical connection portion of the connector unit 16 is detachably connected to the connecting unit 17 with the cap.

An image pickup signal obtained in the image pickup portion is sent to the image processing unit 4 through the connection cable 13 and converted to a video signal by the image processing unit 4. The video signal is displayed on the image display unit 5 as an image picked up by the endoscope 2.

Although the endoscope 2 is an electronic endoscope for picking up an endoscope image by an image pick-up portion (not shown image pick-up device) disposed in the distal end of a later-described insertion portion 21, it may be, for example, a fiber endoscope using an image guide fiber. When the fiber endoscope is used, an optical image guided by the image guide fiber is picked up by a TV camera or the like.

As shown in FIG. 1, the endoscope 2 has a manipulation portion 20 and the insertion portion 21 as a base member.

The universal cord 15 is connected to the manipulation portion 20. A grip portion 22 is disposed in the manipulation portion 20. The manipulation portion 20 is provided with various types of function manipulation members, such as an angle manipulation knob 23, an air/water feed manipulation button 24, a suction manipulation button 25, a gas supply manipulation button 26, and switches 27. The function manipulation members are disposed in portions nearer to a proximal end side than the position of the grip portion 22.

Further, an insertion port 28 of an insertion channel, into which a later-described surgical instrument 40 and the like are inserted, is disposed in a portion which is positioned nearer to a distal end side than the position of the grip portion 22.

As shown in FIG. 1, the insertion portion 21 is composed of a flexible tube (soft portion) 31 positioned to the proximal end side, a bending portion 32 connecting to the distal end of the flexible tube 31, and a distal end portion 33 connected to the distal end of the bending portion 32. The flexible tube 31 has elasticity and flexibility and is bent by an external force. The bending portion 32 is forcibly bend by manipulating the angle manipulation knob 23. The position and the direction of the distal end portion 33 are changed by bending the bending portion 32 so that a desired observation target (affected area and the like) is captured in an observation field of view (or in an image pickup field of view).

As shown in FIG. 1, an observation window 34, an illumination window 35, and a channel port 36 are disposed in the distal end surface portion of the distal end portion 33.

An image pickup unit, which includes an optical system composed of an objective lens (not shown) and the like and an image pick-up device such as a CCD, is disposed inside the observation window 34. The image pick-up unit picks up an affected area and the like in a body cavity. An image pick-up signal obtained by the image pick-up unit is sent to the image processing unit 4 through the connection cable 13 as described above.

The channel port 36 communicates with the insertion port 28 through an insertion channel (not shown) formed in the insertion portion 21. The insertion channel is used as a path through which an insertion portion 42 of a multijointed surgical instrument 40 for an endoscope is inserted.

Although it is assumed in the embodiment that one surgical instrument 40 is inserted into one insertion channel, a plurality of surgical instruments 40 may be inserted into the one insertion channel. Further, it is also possible to provide a plurality of the insertion channels and to insert each of the surgical instruments 40 to each of the insertion channels.

Next, a surgical instrument distal end movement controller 18 will be explained with reference to FIGS. 1, 2, 3A, 3B, and 3C. As shown in FIG. 1, the surgical instrument distal end movement controller 18 includes a surgical instrument controller 37, a surgical instrument drive unit (motor unit) 38, a bending manipulation unit (manipulation input unit) 39, and the surgical instrument 40.

The bending manipulation unit 39 is manipulation mechanism for bending (rotating) the distal end portion 47 in a desired direction.

The surgical instrument 40 includes a manipulation unit 41 which can be gripped by an operator and the insertion portion 42 coupled with the manipulation unit 41.

The surgical instrument drive unit 38 is assembled to the manipulation unit 41.

As shown in FIG. 1, the insertion portion 42 is inserted into a body cavity through the insertion channel. The insertion portion 42 is composed of a flexible tube (soft portion) 45 which is positioned on the proximal end (base end) side, a bending portion 46 connected to the distal end of the flexible tube 45, and a distal end portion (operation arm) 47 connected to the distal end of the bending portion 46. The bending portion 46 may be connected to the distal end of the flexible tube 45.

The flexible tube 45 has elasticity and flexibility and is bent by external force.

The bending portion 46 is bend by the manipulation unit 41.

The distal end portion 47 acts as an end effector (a surgical portion) for operating on an operating portion in a body cavity (for example, an affected area) and the like. To explain in more detail, the distal end portion 47 has a high-frequency surgical instrument. The high frequency surgical instrument is, for example, a high-frequency treatment electrode 118, and a high-frequency knife, a high-frequency solidifier, and the like which are not shown. In the embodiment, the distal end portion 47 as the end effector has the high frequency treatment electrode 118. It is needless to say that the distal end portion 47 may have, for example, a grip forceps 48 to be described later, an electric knife (not shown) and the like.

Figure 2:
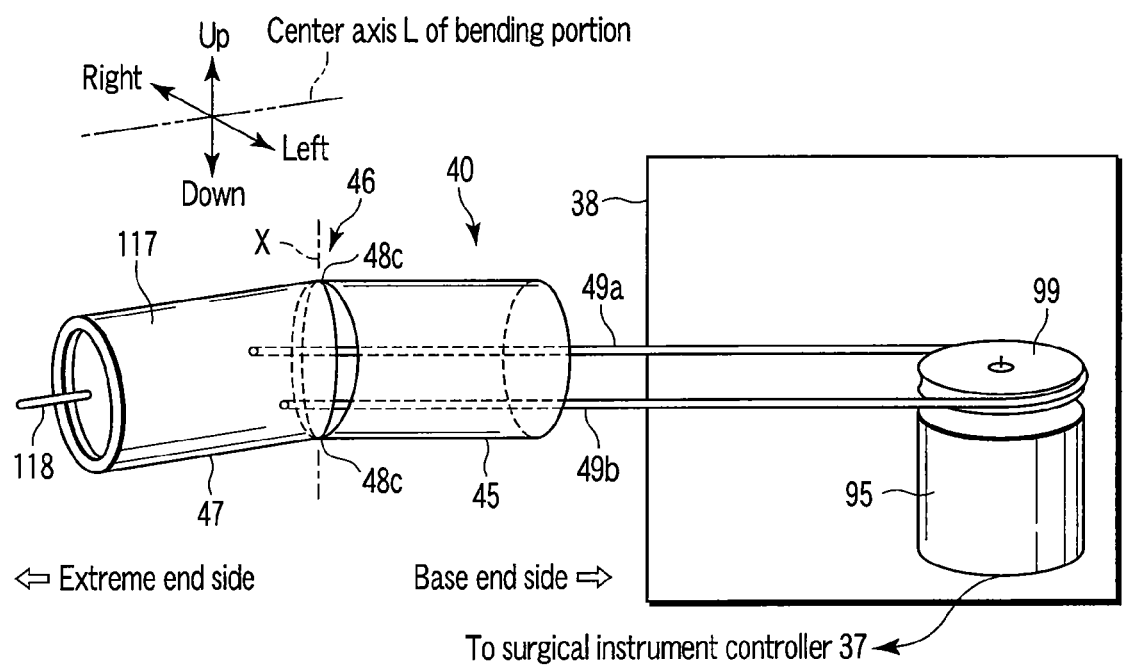
FIG. 2 is an explanatory view schematically showing a surgical instrument drive unit and the surgical instrument of the endoscope system according to the embodiment.

As shown in FIG. 2, the bending portion 46 is rotatably coupled with the distal end portion 47 at a distal end of the flexible tube 45. With this configuration, the bending portion 46 can be bent optionally. The distal end portion 47 can be optionally moved by bending (curving) the bending portion 46. The distal end of the flexible tube 45 (the bending portion 46) is coupled with the distal end portion 47 by a joint 48c. With this configuration, the distal end (the bending portion 46) of the flexible tube 45 and the distal end portion 47 constitute a joint bending mechanism.

Here, the distal end (the bending portion 46) of the flexible tube 45 and the distal end portion 47 can be considered as bending pieces in the joint bending mechanism of the bending portion 46, respectively. The joint 48c has a rotation axis X along an up/down direction shown in FIG. 2. The rotation axis X is orthogonal to a center axis L of the bending portion 46 shown in FIG. 2. Accordingly, the distal end portion 47 is rotated in a right/left direction shown in FIG. 2 with respect to the flexible tube 45.

Further, when the distal end portion 47 is separated to right and left by a plane passing through the rotation axis X and the center axis L, a manipulation wire 49a is connected to a right portion of the distal end portion 47, and a manipulation wire 49b is connected to a left portion thereof. When the pair of manipulation wires 49a, 49b are pushed and pulled, the distal end portion 47 is relatively bent (rotated) in the right/left direction about the rotation axis X by a pulling force of the manipulation wires 49a, 49b. The manipulation wires 49a, 49b pass through the flexible tube 45 and are guided up to the surgical instrument drive unit 38. As described above, the joint bending mechanism is disposed in the insertion portion 42 and moves (rotates) the distal end portion 47 by being bent.

As shown in FIG. 2, the surgical instrument drive unit 38 has a drive motor 95 and a pulley 99 attached to a drive shaft of the drive motor 95. Proximal end portions of the manipulation wires 49a, 49b are trained around the pulley 99. When the drive motor 95 is driven and the pulley 99 is rotated, the manipulation wires 49a, 49b are pushed and pulled in a reverse direction.

Figure 3A:
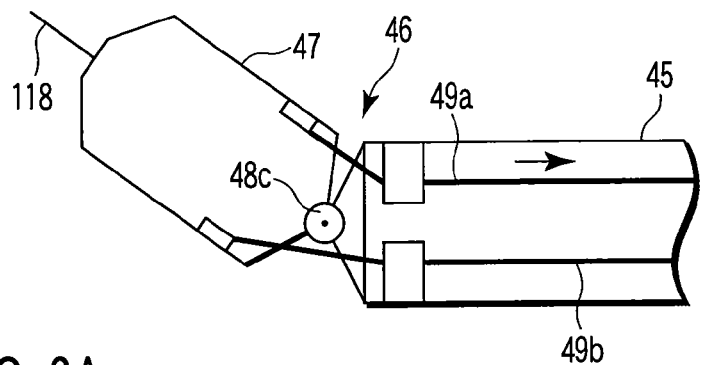
FIG. 3A is an explanatory view showing an operating state of the surgical instrument according to the embodiment.
Figure 3B:
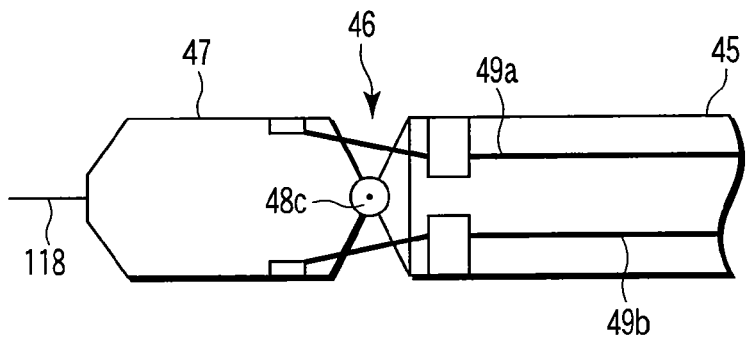
FIG. 3B is an explanatory view showing an operating state of the surgical instrument according to the embodiment.
Figure 3C:
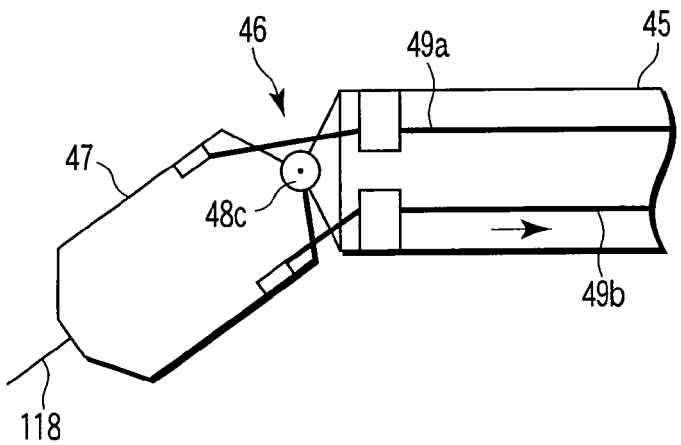
FIG. 3C is an explanatory view showing an operating state of the surgical instrument according to the embodiment.

FIG. 3B shows a state that the distal end portion 47 faces a neutral position. When, for example, the pulley 99 rotates clockwise, the right manipulation wire 49a is pulled as shown in FIG. 3A, and the distal end portion 47 rotates rightward. Further, when, for example, the pulley 99 rotates counterclockwise, the left manipulation wire 49b is pulled as shown in FIG. 3C, and the distal end portion 47 rotates leftward.

As described above, the surgical instrument drive unit 38 is a bending manipulation mechanism which is connected to the surgical instrument 40 and manipulates the bending mechanism (the bending portion 46 and the distal end portion 47).

Although a drive mechanism for pushing and pulling the manipulation wires 49a, 49b is a system making use of the pulley 99, it may be another mechanism making use of, for example, a pinion gear and a rack.

Next, a drive system (the surgical instrument controller 37) for driving the surgical instrument drive unit 38 will be explained. As shown in FIG. 1, the surgical instrument controller 37 is provided with a function control input portion 121 for inputting an instruction output from the bending manipulation unit 39 through a cable 204, a condition for controlling a function of the bending manipulation unit 39, and the like, a motor driver (surgical instrument drive controller) 122 for driving and controlling the drive motor 95, and a motor unit communication unit 123 connected to the surgical instrument drive unit 38 through a cable 201 for executing a communication with the surgical instrument drive unit 38.

The surgical instrument controller 37 transmits a control signal for driving the drive motor 95 in response to a manipulation of the bending manipulation unit 39 executed by an operator to the motor driver 122 and drives the drive motor 95. An encoder (not shown) is attached to the drive motor 95 to measure the number of revolutions thereof. The encoder creates a signal corresponding to the number of revolutions and transfers the signal to the motor driver 122 to thereby execute feedback control of the drive motor 95.

Note that when the bending manipulation unit 39 is manipulated by the operator and the like after a control for moving the surgical instrument 40 is set, a preference is given to an instruction for manipulating the bending manipulation unit 39.

The distal end portion 47 is arranged as a high frequency end effector (surgical portion). Thus, as shown in FIG. 1, the surgical instrument 40 is provided with a power supply line that extends from a surgical instrument high frequency power supply device 113 to the distal end portion 47. The power supply line is a line for supplying high frequency power generated from the power supply device 113 to the distal end portion 47.

A return electrode 115, which comes into contact with a body surface of a patient, and a foot switch 114, which instructs to supply high frequency power to the distal end portion 47 when a foot of the operator and the like is manipulated are connected to the power supply device 113.

Further, the power supply device 113 is provided with a display 161 for displaying how power is supplied and the like, an input panel 162 for inputting the number of output watts, a selection panel 163 for selecting an output mode, and a power output terminal 164.

A cable 165, which supplies high frequency power output from a power supply unit (not shown) disposed inside of the power supply device 113 to the high frequency treatment electrode 118 through the surgical instrument drive unit 38, and a cable 166 for supplying the power to the return electrode 115 are connected to the power output terminal 164. The cable 165 is connected to the high frequency treatment electrode 118 through an electric wire 120 to be described later.

Figure 4:
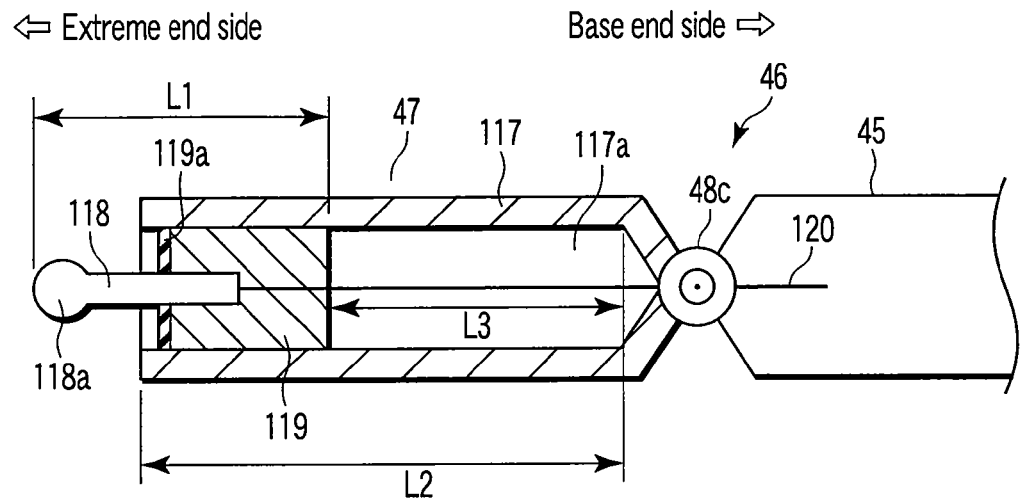
FIG. 4 is a longitudinal sectional view in the vicinity of a distal end portion according to the embodiment.

Next, the distal end portion 47 will be specifically explained. As shown in FIG. 4, the distal end portion 47 has a cylindrical shell 117 formed of an electrically insulating material. An axial direction of an inner hole of the shell 117 is in parallel with the center axis L. Further, a distal end of the inner hole of the shell 117 is opened. The inner hole of the shell 117 forms an accommodation hole (accommodation portion) 117a in which the high frequency treatment electrode 118 can be accommodated (put away). A holding member 119 is accommodated in the accommodation hole 117a so that it can move (slide) forward and backward along the center axis L. The holding member 119 is a moving member (slider) for holding the high frequency treatment electrode 118 and is formed of an electrical insulation member. When the holding member 119 moves forward and backward, the high frequency treatment electrode 118 also moves forward and backward. The high frequency treatment electrode 118 and the accommodation hole 117a are disposed in the distal end portion 47 of the insertion portion 42.

Note that the holding member 119 may be formed of a conductive member. In this case, a distal end of the holding member 119 exposed from (put back) the distal end of the open shell 117 is covered with an insulation member 119a.

The high frequency treatment electrode 118 is formed in a pin-shape. A proximal end of the high frequency treatment electrode 118 is embedded into and fixed (held) to the holding member 119. A distal end of the high frequency treatment electrode 118 projects forward of the open distal end of the holding member 119. Further, the distal end of the high frequency treatment electrode 118 is formed as a spherical portion 118a having a diameter larger than that of the other portion.

As shown in FIG. 4, it is assumed that a portion from a proximal end of the holding member 119 to a distal end of the high frequency treatment electrode 118 (including the spherical portion 118a) has a length "L1" of the end effector (surgical portion). Further, an effective length of the shell 117 is shown by a length "L2" of the shell 117 as an operation arm.

Figure 5:
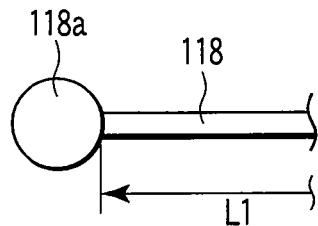
FIG. 5 is an explanatory view showing a high frequency treatment electrode of another surgical instrument according to the embodiment.

Note that when the spherical portion 118a is formed as an electrically insulating distal end tip (when the high frequency treatment electrode 118 is an IT knife electrode) as shown in FIG. 5, the size of L1 is determined from a root of the spherical portion 118a.

Thus, the relation between L1 and L2 is shown by L1<L2. That is, the length L1 of the end effector is shorter than the length L2 of the shell 117. Accordingly, L1<L2 is a condition for allowing the high frequency treatment electrode 118 to be accommodated in the shell 117.

Further, a maximum stroke of the holding member 119 that moves in the shell 117 is set within the range of the length L2 of the shell 117. In more detail, the holding member 119 is drawn into the shell 117 up to a position at which the high frequency treatment electrode 118 is accommodated in the shell 117 in its entirety. For this purpose, for example, a projecting length of the high frequency treatment electrode 118 projecting from the opening distal end of the shell 117 is set to a length of the distal end of the high frequency treatment electrode 118 which is drawn into the shell 117 when the high frequency treatment electrode 118 is accommodated in the shell 117. When the maximum amount of the moving stroke of the holding member 119 is shown by "L3" and L3>L1, the high frequency treatment electrode 118 is drawn into the shell 117 with an allowance.

As described above, the high frequency treatment electrode 118 moves forward to a position at which it is exposed (projected) and a position to and into which it moves backward and is drawn and accommodated in the shell 117.

As described above, the high frequency treatment electrode 118 can be accommodated in a state that it does not come into contact with the insertion channel (not shown) of the endoscope 2, a living body, and the like by being positioned in the shell 117. Accordingly, when the surgical instrument 40 is inserted into and drawn out from the insertion channel of the endoscope 2, the task of inserting and removing the surgical instrument 40 is executed in a state that the high frequency treatment electrode 118 is drawn into and accommodated in the shell 117. That is, even if power is carelessly supplied to the high frequency treatment electrode 118, it is not unintentionally applied to the endoscope 2 and a human body.

Note that power supply check mechanism may be assembled to check the power supplied to the high frequency treatment electrode 118 when the high frequency treatment electrode 118 is accommodated in the shell 117. A method of shutting off a power supply by a switch in association with, for example, a drawing manipulation of the holding member 119 is considered as such power supply check mechanism.

As shown in FIG. 4, a distal end of the electric wire 120, which is a part of the power supply line for supplying high frequency power to the high frequency treatment electrode 118, is connected to the high frequency treatment electrode 118. A proximal end of the electric wire 120 passes through the flexible tube pipe 45 from the bending portion 46 and is connected to the power supply device 113 through the surgical instrument drive unit 38 and the cable 165. The electric wire 120 also acts as a manipulation wire (forward/rearward moving mechanism) for moving the holding member 119 forward and rearward. The high frequency treatment electrode 118 is moved forward and backward as described above by moving the holding member 119 forward and backward by the electric wire 120. The electric wire 120 in the shell 117 is formed as a relatively hard rod-like member. The electric wire 120 from the bending portion 46 is movably guided forward and rearward in the flexible tube 45 by a guide mechanism such as a guide sheath (not shown). Further, the electric wire 120 from the bending portion 46 is connected to the high frequency treatment electrode 118 in the flexible tube 45 and passes through the insertion portion 42 to thereby constitute a manipulation medium which is manipulated by movement manipulation mechanism, to be described later, so as to move forward and rearward.

The electric wire 120 is driven (moved forward and backward) by the movement manipulation mechanism. The movement manipulation mechanism includes a manipulation mechanism 151 and the like. As shown in FIG. 1, the manipulation mechanism 151 is assembled to the surgical instrument drive unit 38. The manipulation mechanism 151 has a rack 152 coupled with the proximal end of the electric wire 120, a pinion gear 153 meshed with the rack 152, and a manipulation lever 154 for rotating the pinion gear 153. When the manipulation lever 154 is rotated by the operator, the pinion gear 153 rotates, the rack 152 moves linearly, the electric wire 120 moves forward and backward, and the holding member 119 moves forward and backward.

That is, the movement manipulation mechanism (the manipulation mechanism 151) is connected to the high frequency treatment electrode 118 through the electric wire 120 as the manipulation medium and moves the high frequency treatment electrode 118 along the inside of the accommodation hole 117*a* to a position at which it is accommodated in the accommodation hole 117*a* and to a position at which it is exposed therefrom as shown in FIG. 4.

It is needless to say that the electric wire 120 may not double as the manipulation wire (forward/rearward manipulation mechanism), and they may be types of using different members. The forward/rearward manipulation mechanism may be assembled to the distal end portion 47. In this case, manipulation control mechanism, which controls the forward/rearward manipulation mechanism, is disposed in a proximal end side of the insertion portion 42. Further, the manipulation control mechanism is disposed in, for example, a manipulation unit 41, and when the manipulation unit 41 is manipulated by a manipulation member such as a handle (function control input unit) 125, the movement manipulation mechanism may be driven.

Figure 6:
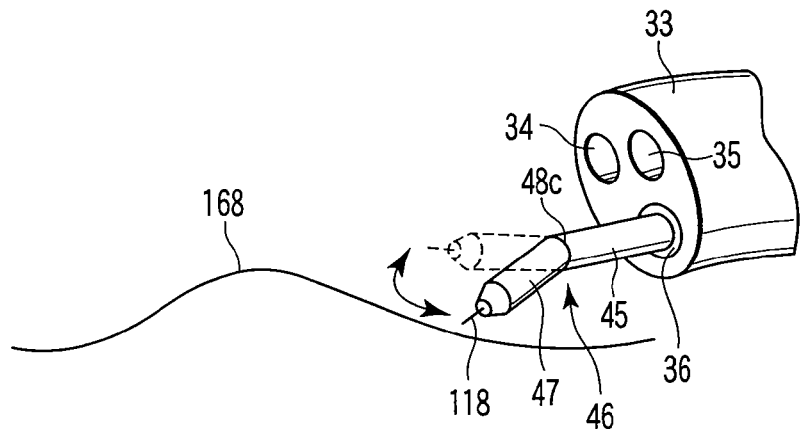
FIG. 6 is a view for explaining how the surgical instrument according to the embodiment is used.

Next, an operation when the surgical instrument 40 is use will be explained. The high frequency treatment electrode 118 is drawn into and accommodated in the shell 117. Next, as shown in FIG. 1, an insertion portion 21 is inserted into a body cavity. The insertion portion 42 is inserted into an insertion port 28. The distal end portion 47 projects from an insertion channel port 36 into the body cavity through the insertion channel (not shown). Thereafter, a high frequency treatment is executed in the body cavity with the surgical instrument 40 (the high frequency treatment electrode 118) while observing it with the endoscope 2. That is, a distal end portion 33 is approached to an affected area 168 by appropriately bending the bending portion 32 as shown in FIG. 6. At this time, the manipulation mechanism 151 is moved from the position at which the high frequency treatment electrode 118 is accommodated in the accommodation hole 117*a* to the position at which it is exposed therefrom as shown in FIG. 4. With this operation, the high frequency treatment electrode 118 projects from the distal end of the open shell 117. When the distal end portion 47 appropriately moves in this state, the high frequency treatment electrode 118 approaches a position of the affected area 168 at which the affected area 168 is desired to be dissected and exfoliated. Then, when high frequency power is supplied from the power supply device 113 to the return electrode 115 and to the high frequency treatment electrode 118 and the bending manipulation unit 39 is manipulated by the operator, the distal end portion 47 is rotated and the affected area 168 is operated.

As shown in, for example, FIG. 6, dissection and exfoliation are executed by swinging the distal end portion 47 in parallel with a mucous membrane of a living body. That is, the distal end portion 47 can be moved (bend) by the bending manipulation unit 39 in a state that the distal end portion 33 approaches the affected area 168. Accordingly, the affected area 168 can be easily dissected and exfoliated.

As described above, the embodiment can move the high frequency treatment electrode 118 to the position at which it is accommodated in the accommodation hole 117*a* and to the position at which it is exposed therefrom as shown in FIG. 4 by the manipulation mechanism 151. Accordingly, in the embodiment, there is no possibility that the insertion channel (not shown) of the endoscope 2 and the like is scratched by the end effector (the high frequency treatment electrode 118) when the surgical instrument 40 is inserted into the insertion channel by accommodating the high frequency treatment electrode 118 in the accommodation hole 117*a*.

Further, when an operation is executed by application of energy such as a high frequency or an ultrasonic wave as in the high frequency treatment electrode 118, the embodiment can avoid operation energy from being carelessly applied to the endoscope 2 and a human body by an unintentional input manipulation when the endoscope 2 is not in an attitude of use.

Further, when the high frequency treatment electrode 118 is accommodated in the accommodation hole 117*a*, it is not in contact with the insertion channel, the living body, and the like. Accordingly, the embodiment can enable the tasks of insertion and removal of the surgical instrument 40 without causing the high frequency treatment electrode 118 to come into contact with the insertion channel and the living body by accommodating the high frequency treatment electrode 118 in the accommodation hole 117*a*.

Further, in the embodiment, even if power is carelessly supplied to the high frequency treatment electrode 118, it can be prevented from being unwillingly applied to the endoscope 2 and the living body by accommodating the high frequency treatment electrode 118 in the accommodation hole 117*a*.

Next, a surgical instrument 40 according to another embodiment will be explained referring to FIGS. 7A, 7B, and 7C. In the surgical instrument 40, an end effector assembled to a distal end portion 47 can be mounted on and dismounted from a holding member 119. That is, the end effector can be replaced with another end effector. The holding member 119 is fitted to and accommodated in a cylindrical shell 117 similar to that of the above embodiment so as to be free to slide forward and backward. A screw portion 174 is formed in a distal end of the holding member 119. Any one of a high frequency treatment electrode unit 172 as shown in FIG. 7B and a grip forceps unit 173 as shown in FIG. 7C is selected and detachably attached to the screw portion 174. The high frequency treatment electrode unit 172 and the grip forceps unit 173 are end effectors. That is, the screw portion 174 is a mounting/dismounting portion for detachably mounting the end effector to the holding member 119.

As shown in FIG. 7B, the high frequency treatment electrode unit 172 is, for example, a pin-like high frequency treatment electrode 175. A proximal end of the high frequency treatment electrode 175 in screwed into the screw portion 174. Accordingly, the high frequency treatment electrode 175 is mounted on the holding member 119.

Further, as shown in FIG. 7C, the grip forceps unit 173 includes a base portion 177, a pair of grip pieces 179a, 179b pivotally connected to the base portion 177, and a manipulation rod 178 coupled with the pair of grip pieces 179a, 179b. A proximal end of the manipulation rod 178 is screwed into the screw portion 174. The base portion 177 is fitted into and attached to a fixing groove 180 formed around an outer periphery at a distal end of the shell 117. Accordingly, the manipulation rod 178 is attached to the holding member 119. When the holding member 119 is moved (slid), the grip pieces 179a, 179b are opened and closed by the manipulation rod 178.

An electric wire 120 is connected to the holding member 119 as in the above embodiment. The electric wire 120 supplies high frequency power to an end effector (surgical portion, high frequency treatment electrode unit 172) attached to the holding member 119. Further, the electric wire 120 also acts as a manipulation wire for manipulating the holding member 119 forward and backward in the shell 117 as in the above embodiment. A push/pull manipulation of the electric wire 120 moves the holding member 119 forward and backward to thereby open and close the grip pieces 179a, 179b.

A manipulation mechanism for manipulating the holding member 119 forward and backward and supply mechanism for supplying the high frequency power to the high frequency treatment electrode 175 are arranged as in the above embodiment. Other configurations and the like are the same as those of the above embodiment.

When the surgical instrument 40 is used as a grip forceps, a grip forceps unit 173 is assembled to the distal end portion 47 as shown in FIG. 7C. Further, when the surgical instrument 40 is used as a high frequency surgical instrument, the high frequency treatment electrode unit 172 is assembled to the distal end portion 47 as shown in FIG. 7B.

Accordingly, the embodiment enables use of the surgical instrument 40 as a grip forceps and as a high frequency treatment electrode. As a result, the embodiment facilitates the work of preparation of operation tools in a hospital, and since it is sufficient to prepare only a certain number of types of end effectors, a stock of operation tools can be simply managed. The embodiment can therefore reduce the overall cost of the operation tools. Further, the embodiment enables mounting of a different end effector by forming a screw portion 174 (mounting/dismounting portion) to a distal end of the holding member 119 which moves with respect to the shell 117.

Next, a surgical instrument 40 according to another embodiment will be explained referring to FIGS. 8A, 8B, 9A, 9B, and 9C.

FIGS. 8A, 8B, 9A, 9B and 9C show another bending portion 46. The bending portion 46 has a manipulation (bending) mechanism for bending a distal end portion (first rod) 47 about a joint 48c with respect to a flexible tube (second rod) 45 and a power generation source (surgical instrument drive unit) for manipulating the manipulation mechanism. The manipulation mechanism and the power generation source are assembled to the flexible tube 45. Other configurations of an endoscope apparatus system are similar to those of the above initially described embodiment.

The flexible tube 45 and the distal end portion 47 constitute a joint bending mechanism by being coupled with each other by the joint 48c.

Here, it can be considered that a distal end of the flexible tube 45 and the distal end portion 47 are bending pieces in the joint bending mechanism of the bending portion 46, respectively. The distal end portion 47 has an accommodation hole 117a disposed thereto in which an end effector (surgical portion) such as a high frequency treatment electrode 118 can be accommodated as shown in FIG. 4 as in the above embodiment.

When the flexible tube 45 and the distal end portion 47 are separated by a center axis (rotation axis X) of the joint 48c and a plane passing through a center axis L to right and left as in the embodiment described above (refer to FIGS. 2 and 3), the manipulation mechanism and the power generation source are assembled to a left portion and to a right portion, respectively.

Figure 9A:
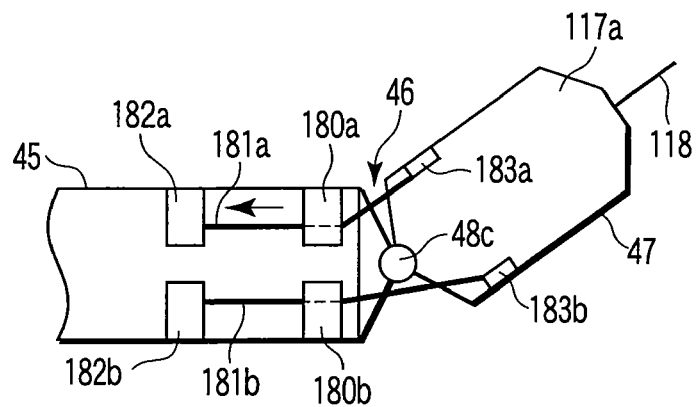
FIG. 9A is a view for explaining how a surgical instrument according to the embodiment is operated.
Figure 9B:
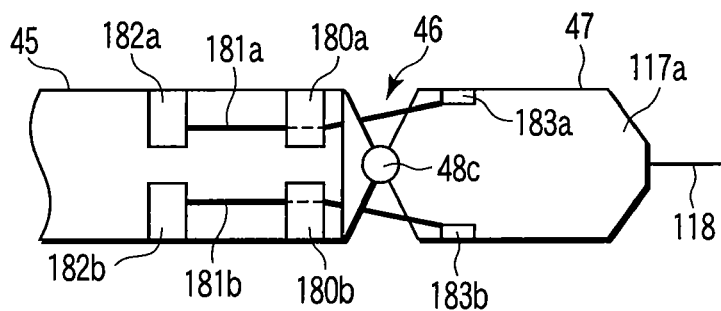
FIG. 9B is a view for explaining how the surgical instrument according to the embodiment is operated.
Figure 9C:
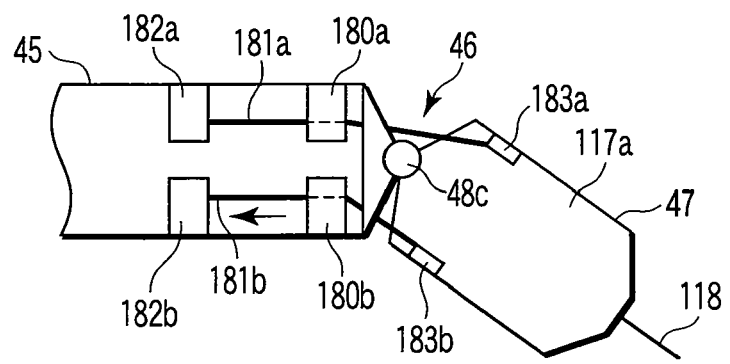
FIG. 9C is a view for explaining how the surgical instrument according to the embodiment is operated.

More specifically, a shape memory alloy wire 181a, which is formed like a wire, is disposed on the left side as shown in FIG. 8A. A shape memory alloy wire 181b, which is formed like a wire, is also disposed on the right side as shown in FIG. 8A. The shape memory alloy wires 181a and 181b are disposed in the distal end portion 47 from the vicinity of a distal end of the flexible tube 45 passing through the bending portion 46. For example, the shape memory alloy wire 181a is a left manipulation mechanism for bending the distal end portion 47 left with respect to the flexible tube 45 about the joint 48c as shown in FIG. 9A and a power generation source for manipulating the left manipulation mechanism. For example, the shape memory alloy wire 181b is a right manipulation mechanism for bending the distal end portion 47 right with respect to the flexible tube 45 about the joint 48c as shown in FIG. 9C and a power generation source for manipulating the right manipulation mechanism.

A distal end of the shape memory alloy wire 181a is fixed to a connecting portion 183a disposed in a left side portion of the distal end portion 47. A distal end of the shape memory alloy wire 181b is fixed to a connecting portion 183b disposed in a right side portion of the distal end portion 47. A proximal end of the shape memory alloy wire 181a is fixed to a connecting portion 182a disposed on a left side portion of the flexible tube 45 through an intermediate guide member 180a disposed in the left side portion of the flexible tube 45. A proximal end of the shape memory alloy wire 181b is fixed to a connecting portion 182b disposed on a right side portion of the flexible tube 45 through an intermediate guide member 180b disposed in the right side portion of the flexible tube 45.

Further, as shown in FIG. 8B, the shape memory alloy wire 181b forms a loop which reaches the connecting portion 183b from the connecting portion 182b through the intermediate guide member 180b and further returns to the connecting portion 182b through the intermediate guide member 180b. Both ends of the loop of the shape memory alloy wire 181b are connected to a power supply electric wire 184 in the connecting portion 182*b*. The power supply electric wire 184 is guided to a proximal end side of an insertion portion 42 through the interior of the flexible tube 45 and connected to a power supply control circuit 185 disposed in, for example, a manipulation unit 20. The power supply control circuit 185 may be disposed outside of the surgical instrument 40. Although not shown, this is the same as to the shape memory alloy wire 181*a*.

A power supplied to the shape memory alloy wires 181*a*, 181*b* is controlled by a manipulation switch (not shown) and the like. When, for example, power is supplied to the shape memory alloy wires 181*a*, it is contracted by generating heat by resistance heating, which bends the distal end portion 47 leftward as shown in FIG. 9A. Further, when, for example, the power is supplied to the shape memory alloy wires 181*b*, it is contracted by generating heat by resistance heating, which bends the distal end portion 47 rightward as shown in FIG. 9C. When the power is not supplied to the shape memory alloy wires 181*a*, 181*b*, they keep the distal end portion 47 at a neutral position as shown in FIG. 9B. Further, an amount of bending of the distal end portion 47 can be adjusted by adjusting a current flowing to the shape memory alloy wires 181*a*, 181*b*.

As described above, in the embodiment, the manipulation mechanism and the power generation source are composed of the shape memory alloy wires 181*a*, 181*b* disposed in the vicinity of the joint 48*c*. Accordingly, the embodiment is configured more simply than a configuration for executing a push/pull manipulation by a manipulation wire guided up to a proximal end side of an insertion portion 42. Further, the end effector of the respective embodiments described above can be assembled to the distal end portion 47 of the embodiment.

Next, an endoscope apparatus system according to another embodiment will be explained based on FIGS. 10, 11, 12A, 12B, 12C, 13A, 13B, 14A, 14B, and 15. Although the overall configuration of the system is approximately the same as those of the embodiments described above, a surgical instrument and its drive system differ in the points described below.

Figure 10:
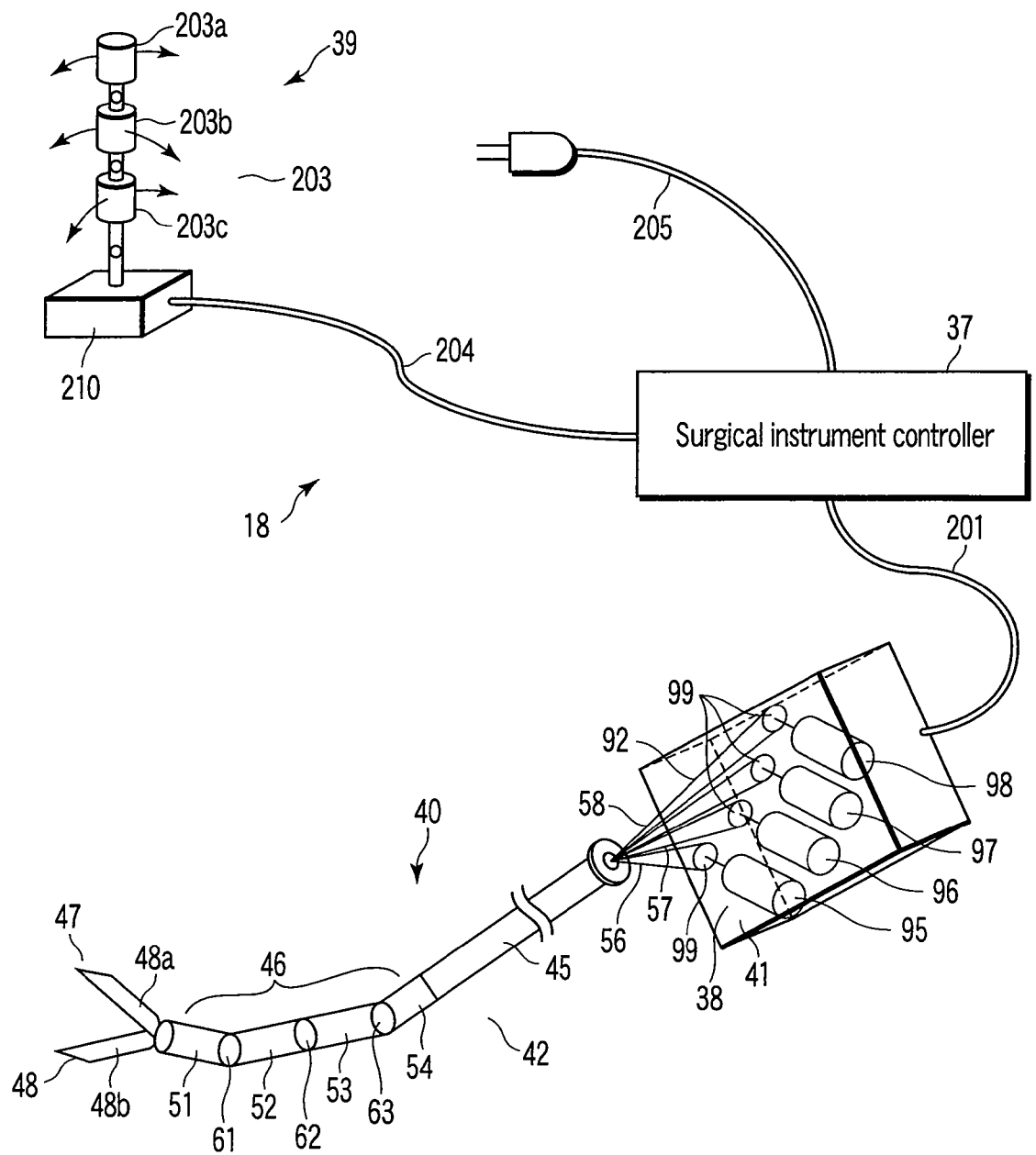
FIG. 10 is a perspective view schematically showing a surgical instrument, a bending manipulation unit and the like in an endoscope apparatus system of another embodiment of the present invention.

First, a surgical instrument distal end movement controller 18 will be explained referring to FIGS. 10, 11, 12A, 12B, and 12C. As shown in FIG. 10, the surgical instrument distal end movement controller 18 includes a surgical instrument controller 37, a surgical instrument drive unit (motor unit) 38, a bending manipulation unit (manipulation input unit) 39, and a surgical instrument 40.

The surgical instrument 40 includes a manipulation unit 41 which can be gripped by an operator and an insertion portion 42 coupled with the manipulation unit 41.

The surgical instrument drive unit 38 is assembled to the manipulation unit 41.

As shown in FIG. 10, the insertion portion 42 is inserted into a body cavity through the insertion channel. The insertion portion 42 is composed of a flexible tube (soft portion) 45 which is positioned on a proximal end (base end) side, a bending portion 46 connected to a distal end of the flexible tube 45, and a distal end portion 47 connected to a distal end of the bending portion 46.

The flexible tube 45 has elasticity and flexibility and is bent by an external force.

The bending portion 46 is bend by the manipulation unit 41.

The distal end portion 47 is provided with a grip forceps 48 as an end effector (surgical portion) for operating on an affected area and the like.

Figure 11:
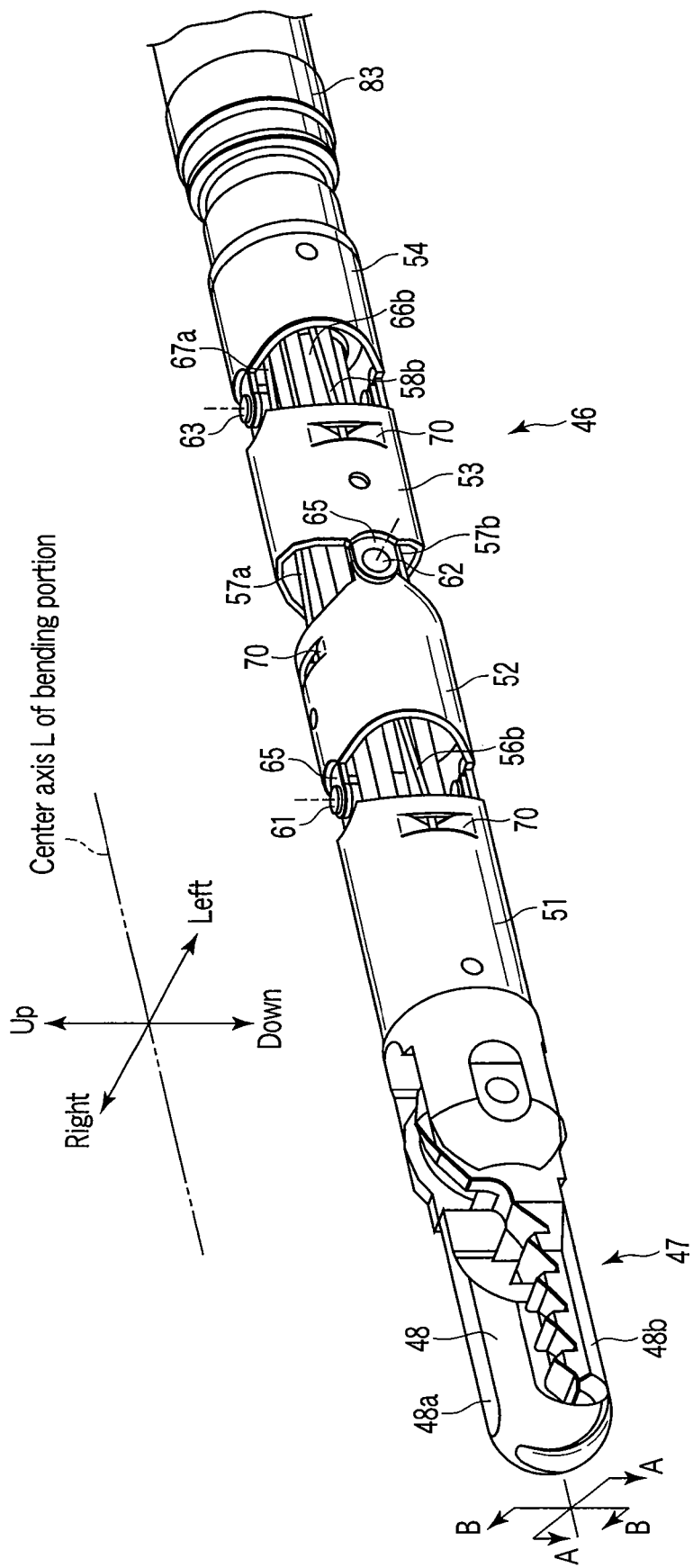
FIG. 11 is a perspective view showing a distal end portion and a bending portion of an insertion portion of the surgical instrument according to the embodiment.

As shown in FIG. 11, the grip forceps 48 includes grip members 48*a*, 48*b* which are opened and closed up and down.

The grip members 48*a*, 48*b* are opened and closed in up and down directions by a manipulation wire 92 inserted into the insertion portion 42. The distal end portion 47 may be provided with an end effector such as a high-frequency knife or a high-frequency solidifier in addition to the grip forceps 48.

Figure 12A:
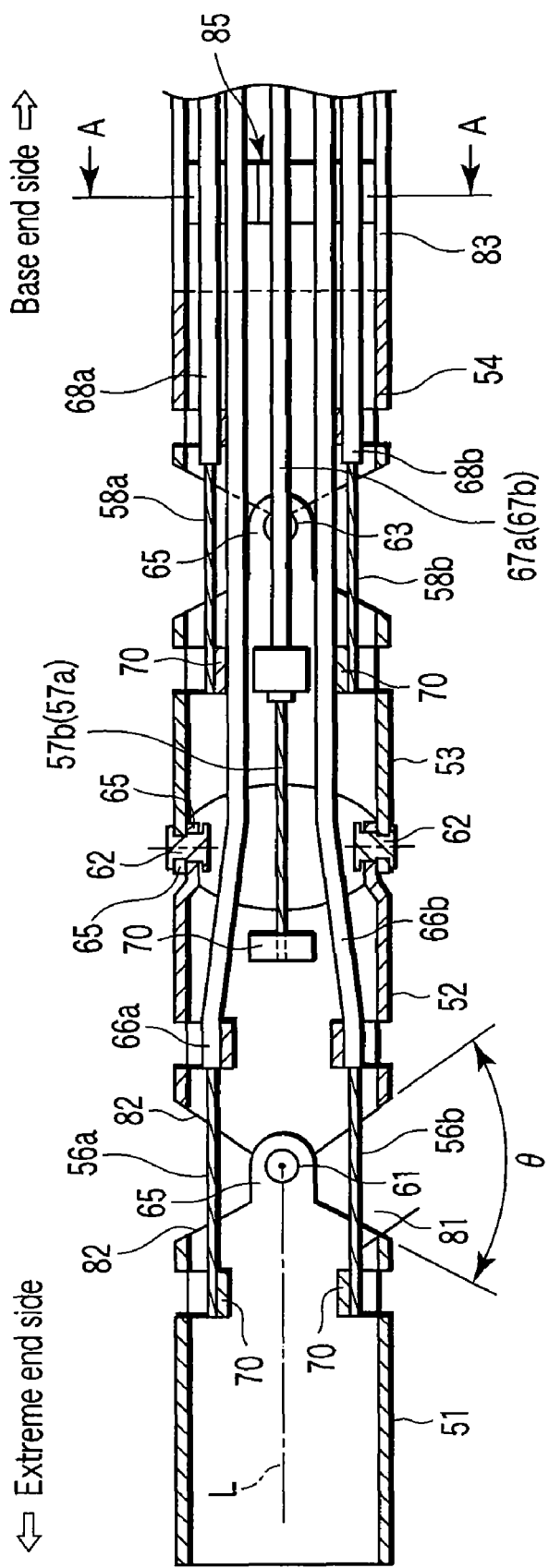
FIG. 12A is a sectional view of a section of the bending portion which is longitudinally sectioned on a horizontal plane shown by an arrow line A-A of FIG. 11 along a long axis direction of an insertion portion and viewed from above it.
Figure 12B:
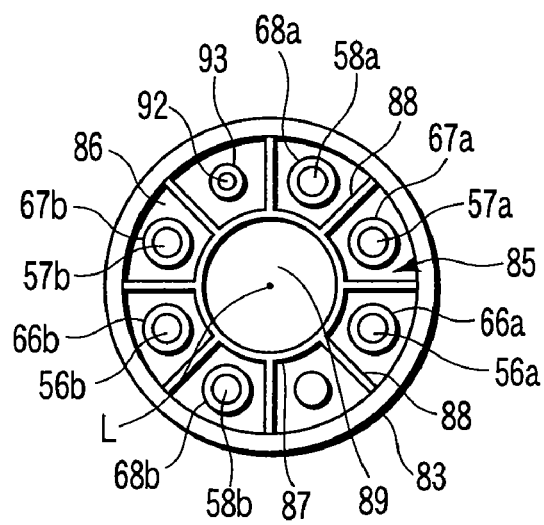
FIG. 12B is a sectional view along the arrow line A-A of FIG. 12A.

As shown in FIGS. 11 and 12A, the bending portion 46 includes a multijointed bending mechanism. The multijointed mechanism is constructed by coupling bending pieces 51, 52, 53, 54. FIG. 11 is a perspective view showing the distal end portion 47 and the bending portion 46. FIG. 12A is a sectional view of a section of the bending portion 46 which is longitudinally sectioned on a horizontal plane shown by an arrow line A-A of FIG. 11 along a long axis direction of the insertion portion 42 and viewed from above it. FIG. 12B is a sectional view along the arrow line A-A in FIG. 12A. Up, down, right, and left directions of the bending portion 46 are as shown by indexes in FIG. 11.

The bending pieces 51, 52, 53, 54 are formed of an annular member. As shown in FIG. 11, the bending pieces 51, 52, 53, 54 are disposed by being coaxially arranged in a line in the long axis direction of the insertion portion 42. The bending pieces 51, 52, 53, 54 are sequentially called a first bending piece 51, a second bending piece 52, a third bending piece 53, and a fourth bending piece 54 from a distal end side thereof.

The first bending piece 51 may constitute the distal end portion. At this time, the first bending piece 51 is provided with an end effector (surgical portion) such as a high frequency treatment electrode 118 and an accommodation portion (for example, an accommodation hole 117*a*) capable of accommodating the surgical instrument as in the embodiment shown in FIG. 4. Further, the first bending piece 51 may be provided with the surgical instrument and the accommodation portion explained in the other embodiments. As described above, the surgical instrument and the accommodation portion may be formed in the first bending piece 51.

The first and second bending pieces 51, 52 are rotatably connected to each other around a first rotation shaft 61 and rotatably coupled with each other by the first rotation shaft 61. The axial direction of the first rotation shaft 61 is orthogonal to the long axis direction of the insertion portion 42 and the first rotation shaft 61 is disposed in a direction along the up and down directions shown in FIG. 11. Accordingly, the first and second bending pieces 51, 52 can be relatively rotate in right and left directions when viewed from the proximal end (base end) side in FIG. 11.

The second and third bending pieces 52, 53 are rotatably connected to each other around a second rotation shaft 62 and rotatably coupled with each other by the second rotation shaft 62. The axial direction of the second rotation shaft 62 is orthogonal to the long axis direction of the insertion portion 42 and the second rotation shaft 62 is disposed in a direction along the right and left directions shown in FIG. 11. Accordingly, the second and third bending pieces 52, 53 can be relatively rotated in the up and down directions when viewed from the proximal end (base end) side in FIG. 11.

The third and fourth bending pieces 53, 54 are rotatably connected to each other around a third rotation shaft 63 and rotatably coupled with each other by the third rotation shaft 63. The axial direction of the third rotation shaft 63 is orthogonal to the long axis direction of the insertion portion 42 and the third rotation shaft 63 is disposed in the direction along the up and down directions shown in FIG. 11. Accordingly, the third and fourth bending pieces 53, 54 can be relatively rotated in the right and left directions when viewed from the proximal end (base end) side in FIG. 11.

That is, the first rotation shaft 61 constitutes a joint for relatively rotating the first and second bending pieces 51, 52 in the right and left directions. The second rotation shaft 62 constitutes a joint for relatively rotating the second and third bending pieces 52, 53 in the up and down directions. The third rotation shaft 63 constitutes a joint for relatively rotating the third and fourth bending pieces 53, 54 in the right and left directions.

In the embodiment, the axial directions of the first, second, and third rotation shafts 61, 62, 63 are alternately offset by 90°. That is, the bending pieces 51, 52 and the bending pieces 53, 54 are rotated in the right and left directions. The bending pieces 52, 53 are rotated in the up and down directions. Further, the axial directions of the rotation shafts 61, 62, 63 are orthogonal to the center axis (long axis) L of the bending portion 46 (refer to FIGS. 11 and 12A). The center axis L agrees with the long axis of the insertion portion 42.

As shown in FIG. 12A, the bending pieces 51, 52, 53, 54 have tongue-piece-shaped coupling portions 65 projecting from the end edges thereof. When the coupling portions 65 are overlapped with each other, the rotation shafts 61, 62, 63 pass through the overlapping portions. That is, the rotation shafts 61, 62, 63 are rivet-like shaft members.

The multijointed bending mechanism arranged as described above is covered with a flexible casing (not shown). The bending portion 46 is constructed by this configuration.

A first set of a pair of non-expandable manipulation wires 56 (56*a*, 56*b*) connected to the first bending piece 51, a second set of a pair of non-expandable manipulation wires 57 (57*a*, 57*b*) connected to the second bending piece 52, and a third set of a pair of non-expandable manipulation wires 58 (58*a*, 58*b*) connected to the third bending piece 53 are inserted into the insertion portion 42.

As shown in FIG. 12A, the manipulation wires 56*a*, 56*b* are laterally symmetrically disposed in the bending portion 46 with respect to the center axis L. The distal ends of the manipulation wires 56*a*, 56*b* extend to the region in the first bending piece 51 and are connected to the first bending piece 51.

The direction of the center axis of the first bending piece 51 approximately agrees with the direction of the center axis L. On one plane which passes through both the direction of the center axis of the first bending piece 51 and the axial direction of the first rotation shaft 61, the right half portion of the first bending piece 51 is called a right portion, and the left half portion of the first bending piece 51 is called a left portion.

The distal end of the manipulation wire 56*a* described above is connected to the right portion of the first bending piece 51. Further, the distal end of the manipulation wire 56*b* is connected to the left portion of the first bending piece 51. When the manipulation wire 56*a* is pulled to the base end (proximal end) side shown in FIG. 12A, the first bending piece 51 is rotated rightward around the first rotation shaft 61. Further, when the manipulation wire 56*b* is pulled to the proximal end side, the first bending piece 51 is rotated leftward around the first rotation shaft 61. As described above, the manipulation wires 56 rotate the first bending piece 51.

As shown in FIG. 12A, the manipulation wires 57*a*, 57*b* are vertically symmetrically disposed in the bending portion 46 with respect to the center axis L. The distal ends of the manipulation wires 57*a*, 57*b* extend to the region in the second bending piece 52 and are connected to the second bending piece 52.

The direction of the center axis of the second bending piece 52 approximately agrees with the direction of the center axis L. On one plane which passes through both the direction of the center axis of the second bending piece 52 and the axial direction of the second rotation shaft 62, the upper half portion of the second bending piece 52 is called an upper portion, and the lower half portion of the second bending piece 52 is called a lower portion.

The distal end of the manipulation wire 57*a* described above is connected to the upper portion of the second bending piece 52. Further, the distal end of the manipulation wire 57*b* is connected to the lower portion of the second bending piece 52. When the manipulation wire 57*a* is pulled to the base end (proximal end) side shown in FIG. 12A, the second bending piece 52 is rotated upward around the second rotation shaft 62. Further, when the manipulation wire 57*b* is pulled to the proximal end side shown in FIG. 12A, the second bending piece 52 is rotated downward around the second rotation shaft 62. As described above, the manipulation wires 57 rotate the second bending piece 52.

As shown in FIG. 12A, the manipulation wires 58*a*, 58*b* are laterally symmetrically disposed in the bending portion 46 with respect to the center axis L. The distal ends of the manipulation wires 58*a*, 58*b* extend in the region of the third bending piece 53 and are connected to the third bending piece 53.

The direction of the center axis of the third bending piece 53 approximately agrees with the direction of the center axis L. On one plane which passes through both the direction of the center axis of the third bending piece 53 and the axial direction of the third rotation shaft 63, the right half portion of the third bending piece 53 is called a right portion, and the left half portion of the third bending piece 53 is called a left portion.

The distal end of the manipulation wire 58*a* described above is connected to the right portion of the third bending piece 53. Further, the distal end of the manipulation wire 58*b* is connected to the left portion of the third bending piece 53. When the manipulation wire 58*a* is pulled to the base end (proximal end) side shown in FIG. 12A, the third bending piece 53 is rotated rightward around the third rotation shaft 63. Further, when the manipulation wire 58*b* is pulled to the proximal end side shown in FIG. 12A, the third bending piece 53 is rotated leftward around the third rotation shaft 63. In this manner, the manipulation wires 58 rotate the third bending piece 53.

As described above, the pairs of the manipulation wires 56, 57, 58, which individually correspond to each other, are connected to the bending pieces 51, 52, 53.

When the pairs of the manipulation wires 56, 57, 58 are appropriately selected and pushed and pulled in the bending portion 46, the bending pieces 51, 52, 53 are independently rotated.

Various methods can be employed to connect the distal ends of the manipulation wires 56, 57, 58 to the bending pieces 51, 52, 53. The connection is made as described below in the embodiment.

As shown in FIG. 12A, in a proximal end portion of the first bending piece 51, cut and raised pieces 70, which project inward of the first bending piece 51, are formed in the right portion and the left portion of the first bending piece 51. The distal end of the manipulation wire 56*a* is inserted into the cut and raised piece 70 in the right portion, and fixed to the cut and raised piece 70 by brazing. Further, the distal end of the manipulation wire 56*b* is inserted into the cut and raised piece 70 in the left portion, and fixed to the cut and raised piece 70 by brazing.

Further, as shown in FIG. 12A, in the proximal end portion of the second bending piece 52, cut and raised pieces 70, which project inward of the second bending piece 52, are formed in the upper portion and the lower portion of the second bending piece 52. The distal end of the manipulation wire 57*a* is inserted into the cut and raised piece 70 in the upper portion and fixed to the cut and raised piece 70 by brazing. Further, the distal end of the manipulation wire 57*b* is inserted into the cut and raised piece 70 in the lower portion and fixed to the cut and raised piece 70 by brazing.

As shown in FIG. 1A, in the periphery of the proximal end portion of the third bending piece 53, cut and raised pieces 70, which project inward of the third bending piece 53, are formed in the right portion and the left portion of the third bending piece 53. The distal end of the manipulation wire 58*a* is inserted into the cut and raised piece 70 in the right portion and fixed to the cut and raised piece 70 by brazing. Further, the distal end of the manipulation wire 58*b* is inserted into the cut and raised piece 70 in the left portion, and fixed to the cut and raised piece 70 by brazing.

The manipulation wires 56 are inserted into a guide sheath 66, the manipulation wires 57 are inserted into a guide sheath 67, and the manipulation wires 58 are inserted into a guide sheath 68, and they are individually guided up to the manipulation unit 41. The guide sheaths 66, 67, 68 have flexibility and are formed of a sheath-like elastic member having elasticity; for example, an intimately wound coil, a resin tube, and the like. The inner holes of the guide sheaths 66, 67, 68 are guide members for guiding the traveling direction of the manipulation wires 56, 57, 58.

The distal end of each guide sheath is connected not to a bending piece to which the manipulation wire to be guided by the guide sheath itself is connected but to a bending piece disposed nearer to the proximal end side than the above bending piece. For example, the distal ends of guide sheaths 66*a*, 66*b* are connected to the second bending piece 52. The distal ends of guide sheaths 67*a*, 67*b* are connected to the third bending piece 53. Further, the distal ends of guide sheaths 68*a*, 68*b* are connected to the fourth bending piece 54.

Figure 13A:
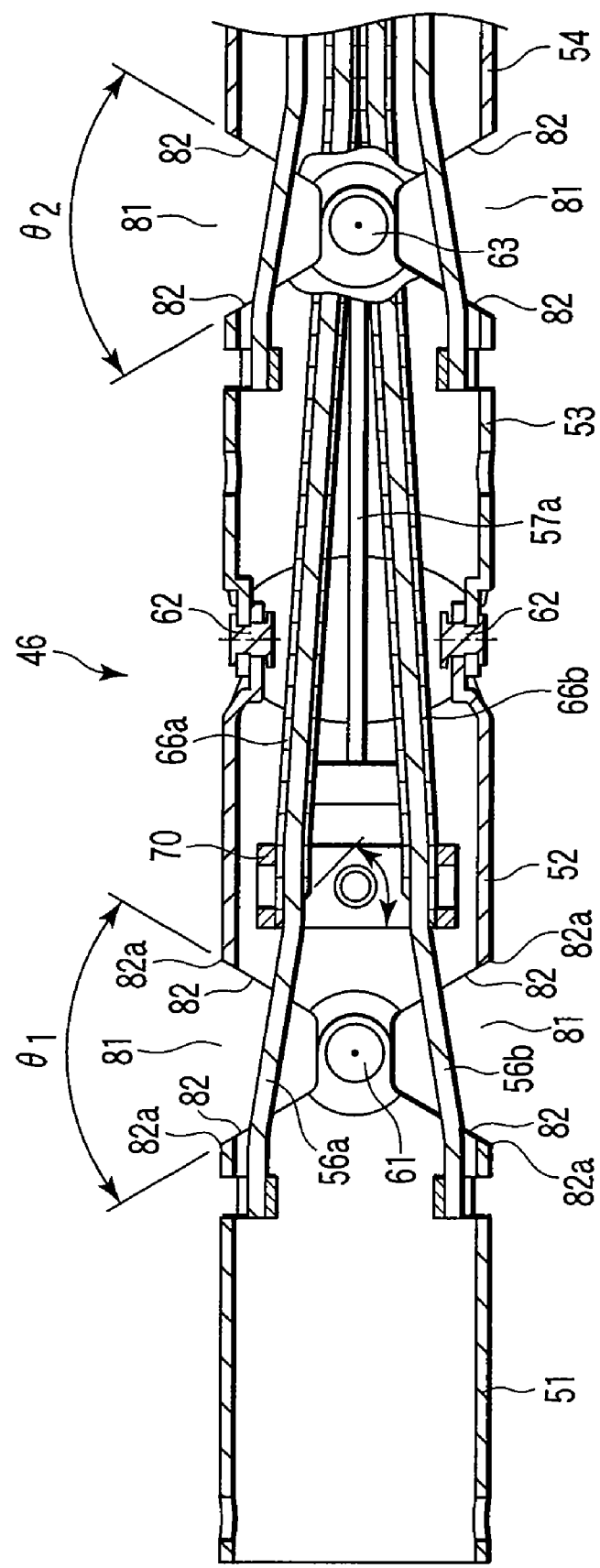
FIG. 13A is a longitudinal sectional view showing the relation of angles at which a bending piece rotates when the bending piece is longitudinally sectioned and viewed from above it.
Figure 13B:
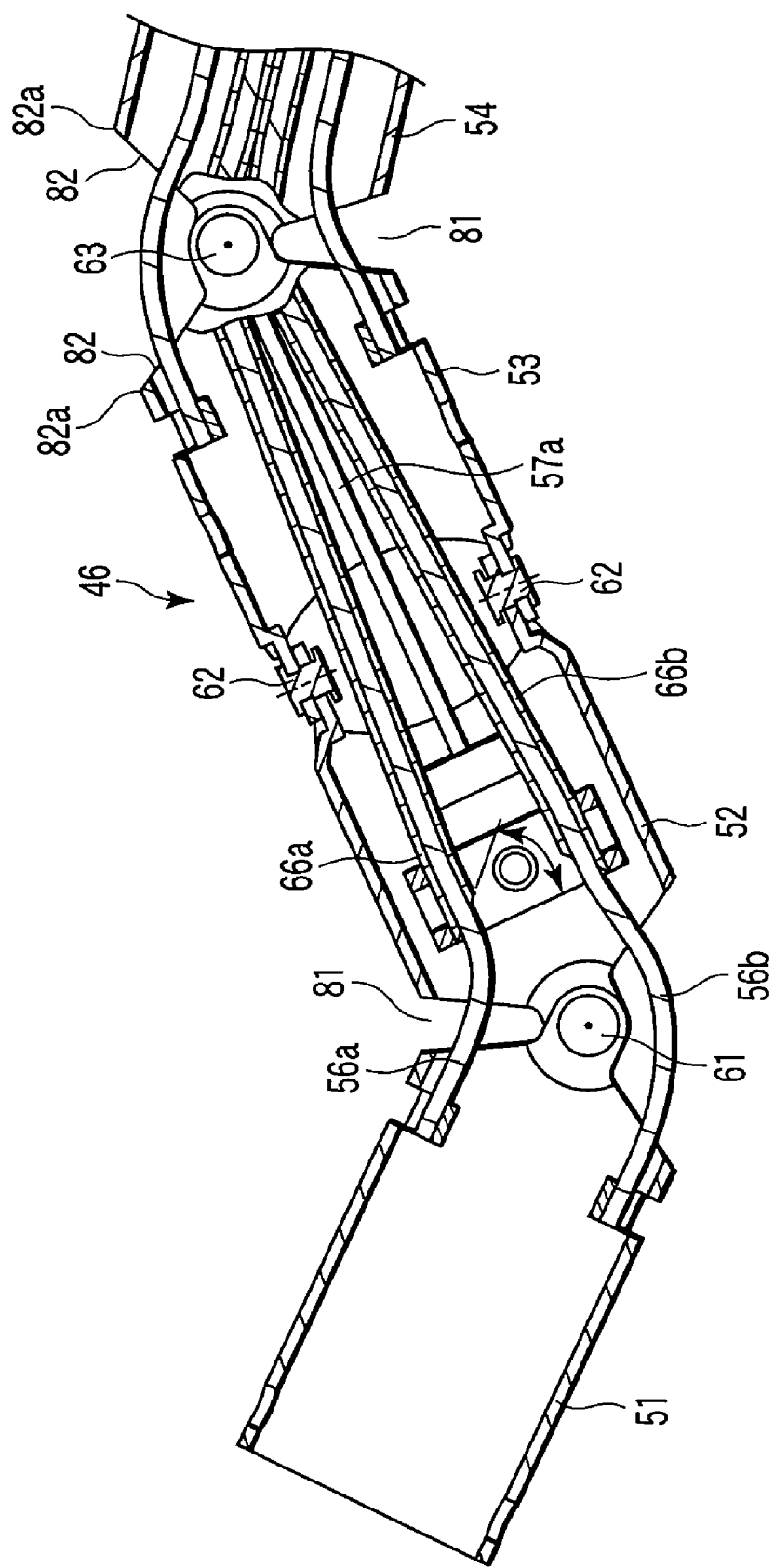
FIG. 13B is a longitudinal sectional view showing the relation of angles at which the bending piece rotates when the bending piece is longitudinally sectioned and viewed from above it.

Note that proximal ends of the guide sheaths may be connected to the proximal end portion of the bending portion 46 (the distal end of the flexible tube 45). Further, as shown in FIGS. 13A and 13B, the most distal end faces of the guide sheaths 66*a*, 66*b* may have slanted surfaces whose sides near the center of the bending portion 46 retreat to the proximal end side than the side thereof near the outer periphery of the bending portion 46. As described above, the guide sheaths 66*a*, 66*b* may be arranged so that they avoid interference with contained members.

Next, the angular relationship under which the respective bending pieces mutually rotate will be explained referring to FIGS. 13A and 13B.

The end faces 82, which confront each other (which are adjacent to each other) in adjacent bending pieces, form a gap 81. The gap 81 expands in a fan-shape at an angle θ about the axis of a rotation shaft. In more detail, lines extending from the end faces 82 intersect on the axis of the rotation shaft. Accordingly, the respective end faces 82 are formed as linear end edges passing through the rotation axis, respectively. Then, the gap 81 is formed by the two end faces 82 confronting each other and expanding in a fan-shape at an angle θ about an intersecting point (axis of the rotation shaft).

Note that the extended lines need not necessarily intersect on the axis of the rotation shaft, and the respective end faces 82 may not be formed as linear end edges passing through the rotation axis, respectively. In this case, the gap 81, which expands in a fan-shape at the angle θ, may be preferably formed by the lines which pass through ends (apexes) 82*a*, which are positioned at the most external sides of the end faces 82, and the axis of the rotation shaft.

Note that the sum of the angles θ of the gaps 81 of at least two adjacent bending pieces in the bending pieces rotating in the same direction is set to 90° or more. As shown in, for example, FIGS. 13A and 13B, the sum of the rotatable angle θ1 of the gap 81 between the bending pieces 51, 52 rotating in the same direction and the rotatable angle θ2 of the gap 81 between the bending pieces 53, 54 rotating in the same direction is set to 90° or more.

As described above, the rotatable angle θ of the multi-jointed bending piece may be preferably allocated not only to one gap 81 but also to the gaps 81 between the bending pieces rotating in the same direction (a plurality of adjacent gaps 81). With this configuration, it is not necessary to increase the angle θ in one gap 81. Accordingly, the maximum angle θ formed by one gap 81 is reduced. As a result, the amount of rotation of a bending piece in one gap 81 is reduced. Thus, when a bending operation causes the contained members such as the manipulation wires and the guide sheaths to traverse the gap 81, they are less likely to be caught by the gap 81.

As shown in FIG. 11, the fourth bending piece 54 is a bending piece positioned at the most extreme proximal end of the bending portion 46. That is, it is possible to assume that the fourth bending piece 54 is the proximal end portion of the bending portion 46. A connector member 83 such as a connection ring is disposed in the distal end of the flexible tube 45. The fourth bending piece 54 is coupled with the connector member 83. Further, the fourth bending piece 54 may be rotatably coupled with the connector member 83. In this mode, it is also possible to assume that the connector member 83 is the proximal end portion of the bending portion 46.

Note that although the fourth bending piece 54 is connected and fixed to the connector member 83, the fourth bending piece 54 need not be limited thereto. When, for example, the number of the bending pieces is increased, a fifth bending piece (not shown) is rotatably connected to the fourth bending piece 54 and further a sixth bending piece (not shown) is rotatably connected to the fifth bending piece so that they are coupled with each other. The sixth bending piece is connected to the connector member 83.

Next, disposition of the manipulation wires and the guide sheaths in the bending pieces and positioning/disposing mechanism will be explained with reference to FIGS. 12B and 12C.

Figure 12C:
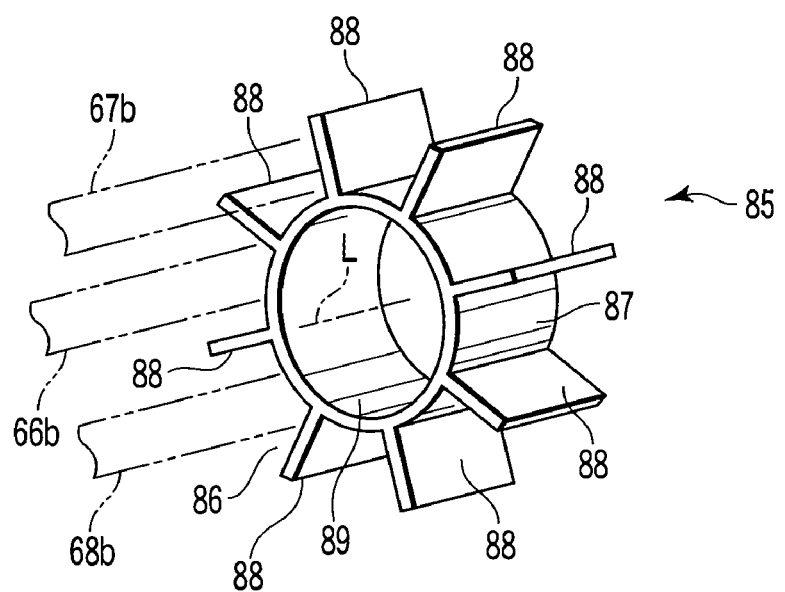
FIG. 12C is a perspective view of a separator.

As shown in FIG. 12A, a frame-like separator 85 shown in FIGS. 12B and 12C is disposed in the connector member 83. The separator 85 is the positioning/disposing mechanism for determining the positions of the manipulation wires and the guide sheaths into which the manipulation wires are inserted. The guide sheaths for guiding the manipulation wires are concentrically disposed around the inner periphery of the bending portion 46 by the separator 85.

Accordingly, the manipulation wires 56, 57, 58 are disposed concentrically in a direction vertical to the axial directions of the first rotating shaft 61, the second rotating shaft 62, and the third rotating shaft 63 (the direction of the center axis L).

In other words, the separator 85 executes positioning so that the manipulation wires 56, 57, 58 are concentrically disposed. The separator 85 may be disposed in the fourth bending piece 54.

As shown in FIG. 12C, the separator 85 has a cylindrical portion 87. A plurality of partition plates 88 are disposed in the outer periphery of the cylindrical portion 87 at approximately the same intervals along the center axis L. The center axis of the cylindrical portion 87 agrees with the center axis L. Further, the partition plates 88 are approximately radially disposed in the center axis of the cylindrical portion 87. Accordingly, a plurality of accommodation paths 86 are formed between the partition plates 88 in the peripheral direction of the cylindrical portion 87. That is, the accommodation paths 86 are concentrically disposed along the peripheral direction of the cylindrical portion 87 around the cylindrical portion 87. The accommodation paths 86 cause the manipulation wires 56, 57, 58 to pass therethrough.

As described above, the separator 85 forms the accommodation paths 86, through which the manipulation wires 56, 57, 58 pass, by the partition plates 88. The separator 85 concentrically positions the manipulation wires 56, 57, 58 by causing them to pass through the accommodation paths 86.

Note that an inner hole of the cylindrical portion 87 is used as an insertion path 89 for inserting contained members and the like thereinto. The insertion path 89 is a space in which other contained members are disposed and positioned in a central region of the insertion portion 42.

As described above, the manipulation wires and the guide sheaths are concentrically positioned and disposed in peripheral portions in the bending portion 46 and the insertion portion 42 by the separator 85.

Further, as shown in FIG. 12B, each set of the manipulation wires and the guide sheaths is separately disposed in the accommodation paths 86. Note that different sets of the manipulation wires and the guide sheaths may be disposed in one accommodation path 86. The manipulation wires and the guide sheaths are guided from the separator 85 up to the manipulation unit 41 through the insertion portion 42.

Further, when the number of the accommodation paths 86 is larger than that of the guide sheaths, the other contained members (for example, a manipulation wire 92 for manipulating the grip forceps 48, a signal line, and the like) are disposed in the accommodation path 86 in which no guide sheath is disposed as shown in FIG. 12B. The manipulation wire 92 is inserted into a guide sheath 93 having flexibility and guided up to the manipulation unit 41 through the flexible tube 45.

As shown in FIG. 10, the manipulation unit 41 is provided with a bending portion manipulation mechanism and an end effector manipulation mechanism. The bending portion manipulation mechanism is provided with drive motors 95, 96, 97 for pushing and pulling the manipulation wires 56, 57, 58, respectively. Further, the end effector manipulation mechanism is provided with a drive motor 98 for pushing and pulling the manipulation wire 92. The manipulation wires 56, 57, 58 correspond to the bending pieces (targets to be rotated) 51, 52, 53 and execute rotating manipulations. The manipulation wire 92 manipulates the grip forceps 48.

Pulleys 99 are attached to drive shafts of the drive motors 95, 96, 97, 98, respectively. The respective drive shafts may be coupled with the respective pulleys 99 through reducers (not shown). The manipulation wires 56, 57, 58, 92 are trained round the respective pulleys 99. The drive motors 95, 96, 97, 98 are individually driven, respectively, and when the pulleys 99 are rotated, the manipulation wires 56, 57, 58, 92 trained around the pulleys 99 are pushed and pulled.

Although the bending portion manipulation mechanism and the end effector manipulation mechanism use transmission mechanisms making use of the pulleys 99, they may use, for example, a gear mechanism and the like making use of a pinion gear and a rack. Further, the bending portion manipulation mechanism and the end effector manipulation mechanism may use other types of drive actuators in place of the drive motors 95, 96, 97, 98.

As shown in FIG. 10, the manipulation unit 41 is connected to the surgical instrument controller 37 through a cable 201. The bending manipulation unit 39 as the manipulation input unit is connected to the surgical instrument controller 37 through a cable 204. In FIG. 10, the surgical instrument controller 37 is provided with a power supply cord 205.

The bending manipulation unit 39 includes a joystick (manipulation input unit) 203 for instructing a position and an attitude of the surgical instrument 40. The joystick 203 includes three joystick switches 203a, 203b, 203c continuously connected in three stages. The joystick switches 203a, 203b, 203c are attached to a manipulation box 210.

When the joystick switches 203a, 203b, 203c are selectively manipulated, the drive motors 95, 96, 97 are individually driven corresponding to the manipulation. With this manipulation, the bending pieces 51, 52, 53 are individually and independently driven in up, down, right, and left directions to thereby bend respective joint portions.

The surgical instrument distal end movement controller 18 can move the distal end portion 47 to a desired position by the movement according to the manipulation of the joystick 203. That is, the surgical instrument distal end movement controller 18 constitutes the surgical instrument 40 which is arranged as a master/slave type and is driven electrically. Note that, when the joystick 203 is manipulated by an operator and the like after a control for moving the surgical instrument 40 is set, preference is given to an instruction for manipulating the joystick 203.

As shown in FIG. 1, the surgical instrument controller 37 is provided with a function control input portion 121 for inputting an instruction output from the joystick 203, a condition for controlling the function of the joystick 203, and the like, a motor driver (surgical instrument drive controller) 122 for controlling the drive of the drive motors 95, 96, 97, and a motor unit communication unit 123 connected to the surgical instrument drive unit 38 through the cable 201 for executing communication with the surgical instrument drive unit 38.

The surgical instrument controller 37 transmits a control signal for driving the drive motors 95, 96, 97 in response to the manipulation of the joystick 203 executed by the operator to the motor driver 122 and rotates the drive motors 95, 96, 97. Encoders (not shown) are mounted on the drive motors 95, 96, 97 to measure the numbers of revolutions thereof. The encoders feedback-control the drive motors 95, 96, 97 by generating signals according to the number of revolutions and transmitting the signals to the motor driver 122.

The relation between a multijointed structure in the bending portion 46 and the joystick 203 will be explained referring to FIGS. 14A, 14B and 15.

As shown in FIG. 14A, in a state that all the joint portions in the bending portion 46 project from the distal end portion 33, the joints disposed from the manipulation unit side (proximal end side) to the distal end side are sequentially referred to as J1, J2, J3. A coordinate system is set using the joint J1 disposed nearest to the manipulation unit side as a reference. In the coordinate system, a Y-axis direction agrees with a vertical direction of the image pickup device. It is assumed that the joints J1, J3 are bent about an X-axis, and the joint J2 is bent about a Y-axis.

As shown in FIG. 15, the joystick 203 (manipulation input unit) includes joints J1', J2', J3' which have the same structures as those of the joint J1 and the joints J2, J3 located nearer to the distal end side than the joint J1.

The number of the joints and the bending directions of the joystick 203 are the same as those of the bending portion 46. The lengths of respective rods of the joystick 203 are set to values multiplied by an appropriate coefficient k so that the operator can easily manipulate them. When, for example, k=10 and the length of each rod of the surgical instrument 40 is 3 mm, the length of each rod of the joystick 203 (manipulation input unit) is set to 30 mm. Encoders (not shown) are assembled to the joints J1', J2', J3' to measure bent angles. The information of the bent angles measured by the encoders is sent to the surgical instrument controller 37. The surgical instrument controller 37 generates drive signals corresponding to the angle information (the joints J1', J2', J3') and bends the joints J1, J2, J3 by rotating the drive motors 95, 96, 97, respectively. When the joints J1', J2', J3' are bent as shown in, for example, FIG. 15, the joints J1, J2, J3 are bent as shown in FIG. 14B.

Since the bending portion 46 has a plurality of joints, the distal end of the surgical instrument 40 can be moved to an arbitrary position and an arbitrary attitude so that an affected area can be more easily cut out and exfoliated than ever before. Further, since the joint structure of the surgical instrument 40 is caused to equally correspond to that of the manipulation input unit, the operator can easily operate the surgical instrument having a plurality of joints.

Further, the drive motor 98 also has a motor driver, a motor unit communication unit, and the like similarly to the drive motors 95, 96, 97. The grip forceps 48 is manipulated by manipulating a manipulation body such as a handle (function control/input unit) 125 disposed in the manipulation unit 41 and the like.

Note that the manipulation input unit may be preferably provided with a first manipulation switch corresponding to the first bending piece 51, a second manipulation switch corresponding to the second bending piece 52, a third manipulation switch corresponding to the third bending piece 53, and a fourth manipulation switch corresponding to the fourth bending piece 54. When, for example, the first manipulation switch is depressed, the first bending piece 51 is bent. Further, the manipulation unit 41 may be preferably provided with a switch device (manipulation switch) for the bending manipulation. The manipulation input unit may use a pen type input unit for inputting a three-dimensional position.

Next, an operation when the surgical instrument 40 is used will be explained.

First, the insertion portion 21 is inserted into a body cavity, and the insertion portion 42 is inserted from the insertion port 28 into the insertion channel in this state. The distal end portion 47 and the bending portion 46 project from the channel port 36 into the body cavity. Then, a work for gripping an affected area and the like in the body cavity is executed using the grip forceps 48 while observing them by the endoscope 2.

In this case, the bending portion 46 can be bend to an appropriate multijointed bent shape according to the state in the body cavity and the surgical procedure. That is, when the joystick 203 is manipulated and the bending pieces 51, 52, 53 are individually rotated, the bending portion 46 is bend into an appropriate shape.

When, for example, the drive motor 95 is driven, the manipulating wires 56a, 56b trained around the pulley 99 in the drive motor 95 are pushed and pulled. With this operation, the first bending piece 51 is independently rotated. When the drive motor 96 is driven, the manipulation wires 57a, 57b trained around the pulley 99 in the drive motor 96 are pushed and pulled. With this operation, the second bending piece 52 is independently rotated. Further, when the drive motor 97 is driven, the manipulation wires 58a, 58b trained around a pulley 99 in the drive motor 97 are pushed and pulled. With this operation, the third bending piece 53 is independently rotated.

Accordingly, when the joystick 203 is appropriately operated, the bending pieces 51, 52, 53 are independently rotated, and the bending portion 46 is bent. The bending portion 46 can even be bend in a complex shape by adjusting the direction in which the joystick 203 is rotated and the amount of rotation thereof.

As described above, in the embodiment, since the manipulation wires are disposed in the plurality of bending pieces, only an arbitrary bending piece can be independently rotated. Accordingly, in the embodiment, since the bending mechanism has a plurality of degrees of freedom, a work can be executed even in a narrow region such as a body cavity.

In more detail, in the embodiment, since the bending pieces 51, 52, 53 can be independently rotated (bend), the bending portion 46 can be partially bent also in a different direction. Thus, in the embodiment, the bending portion 46 can be bent into an appropriate shape according to a state of use. As a result, since the degree of freedom of bending of the bending portion 46 is increased, it is possible in the embodiment to easily execute even a complex work in a narrow body cavity region as compared with a case in which the bending portion 46 is uniformly bent. Further, in the embodiment, since the attitude of the bending portion 46 can be easily bent so that it does not disturb other surgical instrument and observation with the endoscope 2, the workability of the surgical instrument 40 can be increased.

Further, in the embodiment, since the plurality of wires are concentrically disposed in the bending pieces, the plurality of manipulation wires can be disposed compactly in the bending pieces. Accordingly, the embodiment can avoid complicated disposition in which the plurality of manipulation wires are entangled with each other. Further, the embodiment can form the space in the bending pieces in which the other contained members are disposed.

To explain in detail, in the embodiment, the manipulation wires 56, 57, 58 and the guide sheaths 66, 67, 68 are inserted into the accommodation paths 86 and concentrically disposed therein. Accordingly, in the embodiment, the manipulation wires 56, 57, 58 can be disposed without being entangled with each other even though they are inserted into the narrow bending portion 46, and further the manipulation wires 56, 57, 58 can be disposed compactly. In other words, in the embodiment, since the manipulation wires 56, 57, 58 can be prevented from being entangled in the bending portion 46, occurrence of mutual interference of the manipulation wires can be reduced. In the embodiment, disturbance of transmission of the manipulation force of the manipulation wires 56, 57, 58 can be prevented. Since the embodiment can obtain an allowance for disposing the other contained member in the bending portion 46, the diameter of the bending portion 46 can be reduced.

Further, in the embodiment, the manipulation wires 56, 57, 58 are concentrically disposed. Accordingly, the embodiment can form the insertion path 89 as the space in the bending pieces in which the other contained members are installed.

Further, in the embodiment, a guide sheath, which guides a manipulation wire for rotating a bending piece, is connected to a bending piece located just behind the above bending piece (on the proximal end side). Thus, the embodiment can maximize the efficacy of the wire guide function achieved by the guide sheath. Further, the region in which the manipulation wires are separately exposed can be reduced. Accordingly, the embodiment can avoid any effect on the wire guide functionality. Further, when, for example, the insertion portion 42 itself is twisted, the embodiment can alleviate the effect of the twist on the wire guide function of the guide sheaths.

Further, in the embodiment, the guide sheaths may be formed of an intimately wound metal coil. With this configuration, the embodiment can sufficiently withstand the abrupt rotating and bending actions of the bending pieces.

Next, an endoscope apparatus system according to another embodiment will be explained based on FIGS. 16, 17, 18A, 18B, 19A, 19B, 19C, 19D, 20A, 20B and 21. Although an overall configuration of the system is approximately the same as those of the embodiments described above, a surgical instrument and its drive system differs in the points described below.

Figure 16:
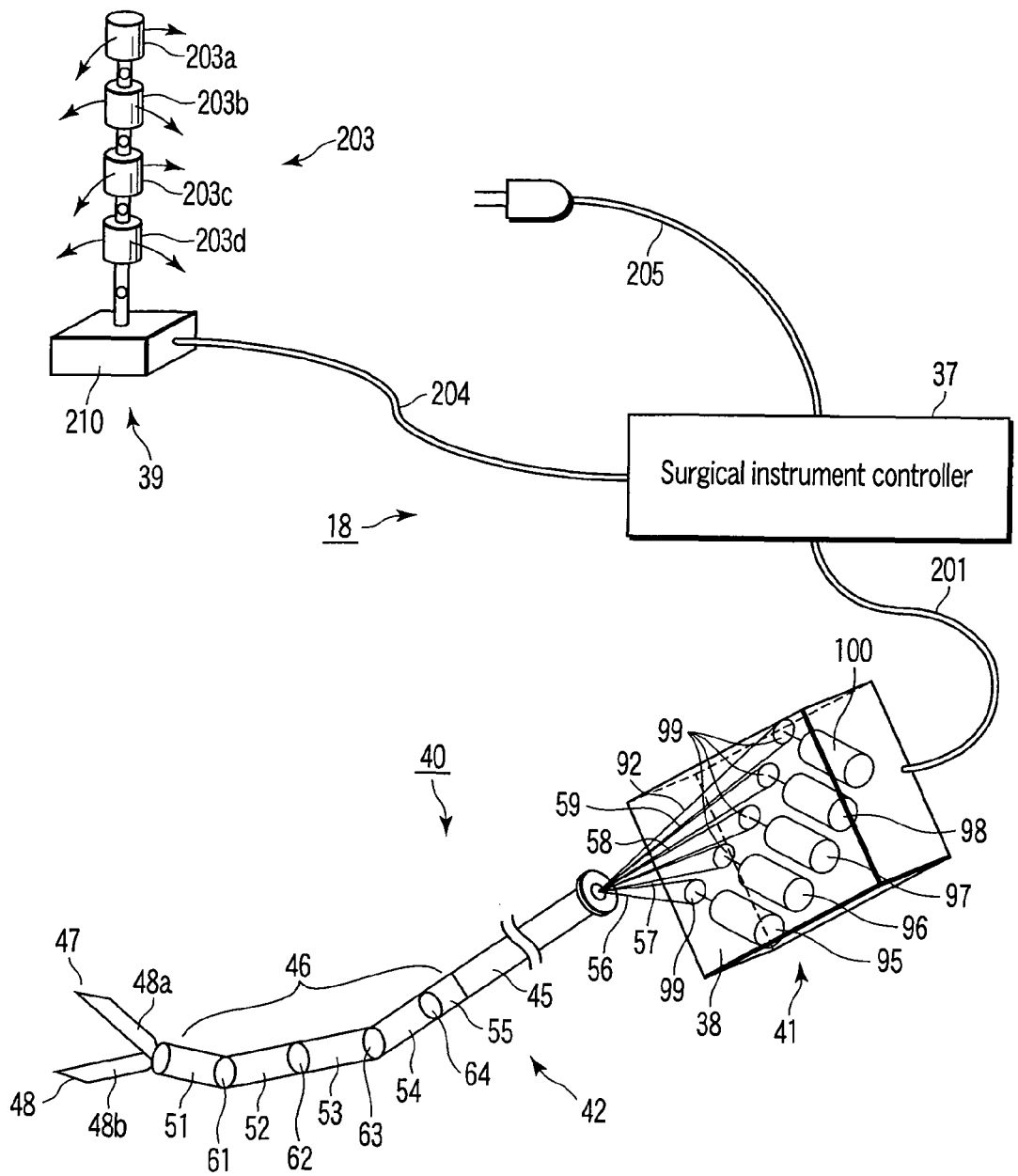
FIG. 16 is a perspective view schematically showing a surgical instrument, a bending manipulation unit and the like in an endoscope apparatus system of another embodiment of the present invention.

First, a surgical instrument distal end movement controller 18 will be explained referring to FIGS. 16, 17, 18A, 18B, 19A, 19B, 19C and 19D. As shown in FIG. 16, the surgical instrument distal end movement controller 18 includes a surgical instrument controller 37, a surgical instrument drive unit (motor unit) 38, a bending manipulation unit (manipulation input unit) 39, and a surgical instrument 40.

The surgical instrument 40 includes a manipulation unit 41 which can be gripped by an operator and the insertion portion 42 coupled with the manipulation unit 41.

The surgical instrument drive unit 38 is assembled to the manipulation unit 41.

As shown in FIG. 16, the insertion portion 42 is inserted into a body cavity through the insertion channel. The insertion portion 42 is composed of a flexible tube (soft portion) 45 which is positioned on the proximal end (base end) side, a bending portion 46 connected to the distal end of the flexible tube 45, and a distal end portion 47 connected to a distal end of the bending portion 46.

The flexible tube 45 has elasticity and flexibility and is bent by an external force.

The bending portion 46 is bent by the manipulation unit 41.

The distal end portion 47 is provided with a grip forceps 48 as an end effector for operating on an affected area and the like.

Figure 17:
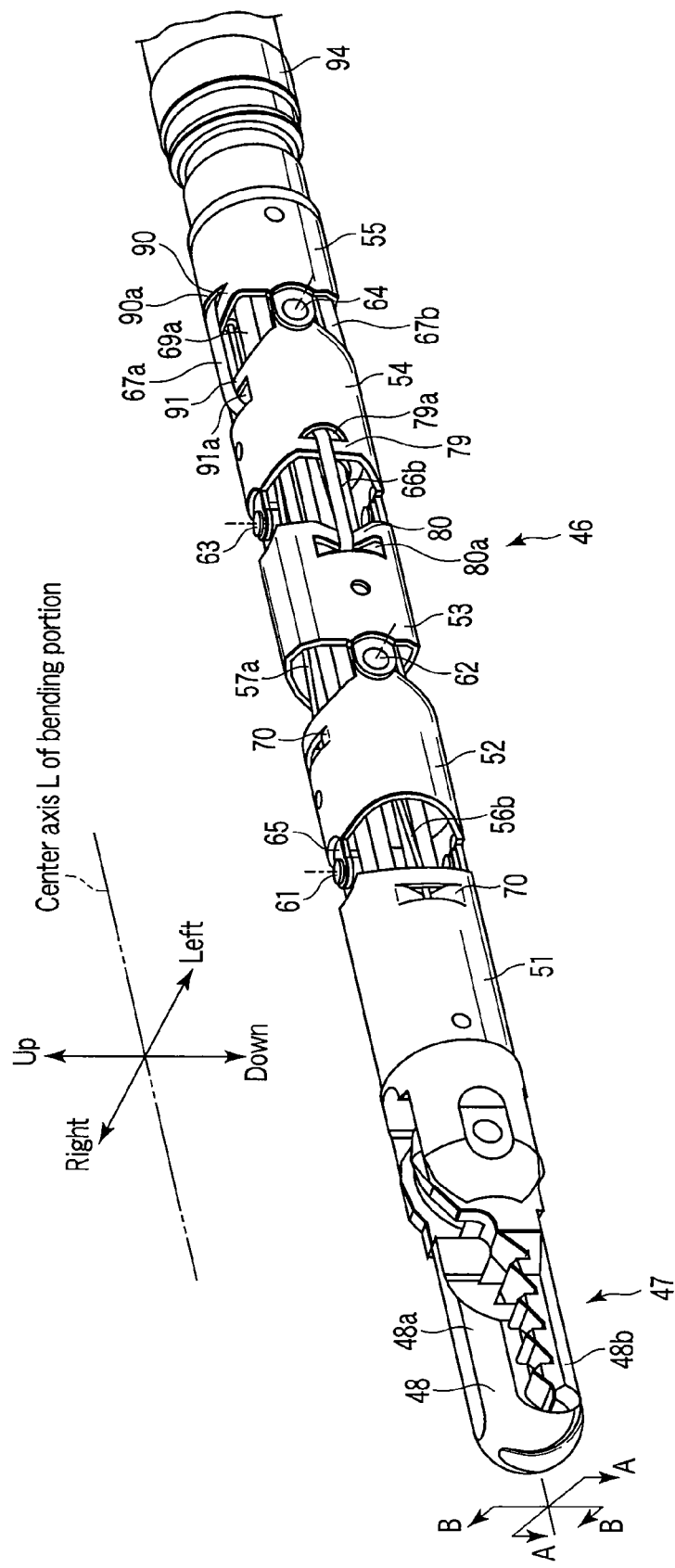
FIG. 17 is a perspective view showing a distal end portion and a bending portion of an insertion portion of a surgical instrument according to the embodiment.

As shown in FIG. 17, the grip forceps 48 includes grip members 48a, 48b which are opened and closed up and down. The grip members 48a, 48b are opened and closed in up and down direction by a manipulation wire 92 inserted into the insertion portion 42. The distal end portion 47 may be provided with a surgical instrument such as a high-frequency knife or a high-frequency solidifier in addition to the grip forceps 48.

Figure 18B:
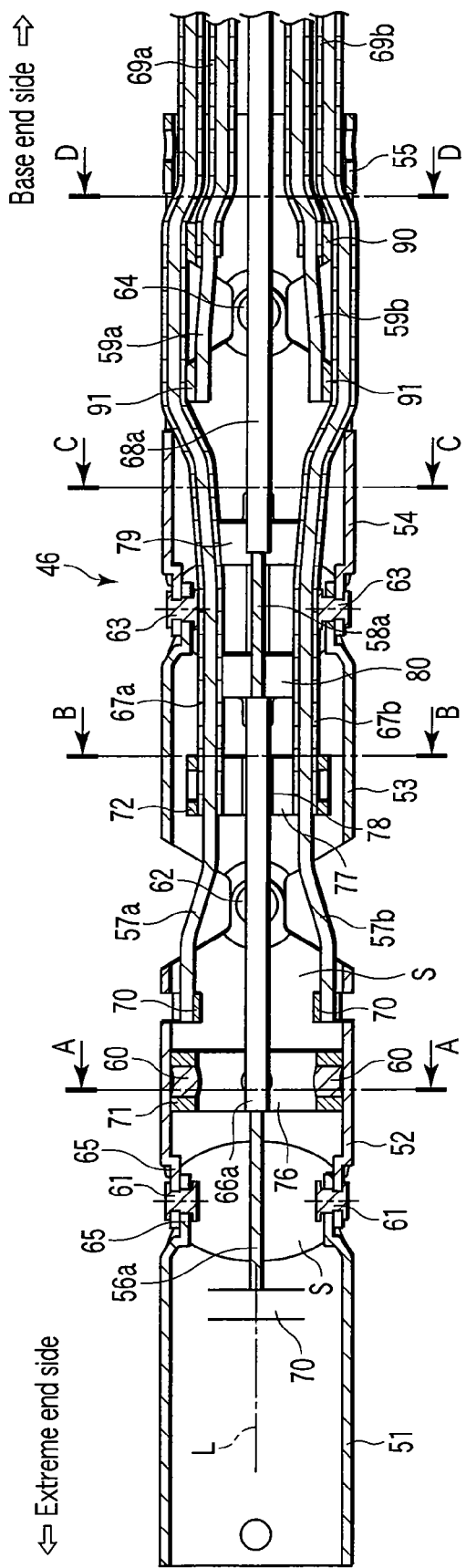
FIG. 18B is a sectional view of a section of the bending portion which is longitudinally sectioned on a vertical plane shown by an arrow line B-B of FIG. 17 along the long axis direction of the insertion portion and viewed from a left side.

As shown in FIGS. 17, 18A and 18B, the bending portion 46 includes a multijointed bending mechanism. The multijointed mechanism is configured by coupling bending pieces 51, 52, 53, 54, 55. FIG. 17 is a perspective view showing the distal end portion 47 and the bending portion 46. FIG. 18A is a sectional view of a section of the bending portion 46 which is longitudinally sectioned on a horizontal plane shown by an arrow line A-A of FIG. 17 along a long axis direction of the insertion portion 42 and viewed from above it. FIG. 18B is a sectional view of a section of the bending portion 46 which is longitudinally sectioned on a vertical plane shown by an arrow line B-B of FIG. 17 along a long axis direction of the insertion portion 42 and viewed from a left side. Up, down, right, and left directions of the bending portion 46 are as shown by an index in FIG. 17.

The bending pieces 51, 52, 53, 54 are formed of an annular member. As shown in FIG. 17, the bending pieces 51, 52, 53, 54, 55 are disposed by being coaxially arranged in line in the long axis direction of the insertion portion 42. The bending pieces 51, 52, 53, 54, 55 are sequentially called a first bending piece 51, a second bending piece 52, a third bending piece 53, a fourth bending piece 54, and a fifth bending piece 55 from a distal end side thereof.

The first bending piece 51 may constitute the distal end portion. At this time, the first bending piece 51 is provided with the end effector such as the high frequency treatment electrode 118 and the accommodation hole 117a capable of accommodating the end effector as shown in FIG. 4. Further, the first bending piece 51 may be provided with the surgical instrument and the accommodation portion explained in the other embodiments. As described above, the surgical instrument and the accommodation portion may be formed in the first bending piece 51.

As shown in FIG. 17, the first bending piece 51 is relatively rotatably coupled with the second bending piece 52 by the first rotation shaft 61 having a rotation shaft. As shown in FIG. 18B, the rotation shaft of the first rotation shaft 61 is disposed so as to be orthogonal to the center axis L of the bending portion 46 as well as in a direction along the up/down direction.

The first and second bending piece 51, 52 are rotatably connected to each other around a first rotation shaft 61 and rotatably coupled with each other by the first rotation shaft 61. The axial direction of the first rotation shaft 61 is orthogonal to the long axis direction of the insertion portion 42 and the first rotation shaft 61 is disposed in a direction along the up and down direction shown in FIG. 17. Accordingly, the first and second bending pieces 51, 52 can be relatively rotate in right and left direction when viewed from the proximal end (base end) side in FIG. 17.

The second and the third bending piece 52, 53 are rotatably connected to each other around a second rotation shaft 62 and rotatably coupled with each other by the second rotation shaft 62. The axial direction of the second rotation shaft 62 is orthogonal to the long axis direction of the insertion portion 42 and the second rotation shaft 62 is disposed in a direction along the right and left direction shown in FIG. 17. Accordingly, the second and third bending pieces 52, 53 can be relatively rotate in the up and down direction when viewed from the proximal end (base end) side in FIG. 17.

The third and the fourth bending piece 53, 54 are rotatably connected to each other around a third rotation shaft 63 and rotatably coupled with each other by the third rotation shaft 63. The axial direction of the third rotation shaft 63 is orthogonal to the long axis direction of the insertion portion 42 and the third rotation shaft 63 is disposed in the direction along the up and down direction shown in FIG. 17. Accordingly, the third and fourth bending pieces 53, 54 can be relatively rotate in the right and left direction when viewed from the proximal end (base end) side in FIG. 17.

The fourth and the fifth bending piece 54, 55 are rotatably connected to each other around a fourth rotation shaft 64 and rotatably coupled with each other by the fourth rotation shaft 64. The axial direction of the fourth rotation shaft 64 is orthogonal to the long axis direction of the insertion portion 42 and the fourth rotation shaft 64 is disposed in the direction along the right and left direction shown in FIG. 17. Accordingly, the fourth and fifth bending pieces 54, 55 can be relatively rotate in the up and down direction when viewed from the proximal end (base end) side in FIG. 17.

That is, the first rotation shaft 61 constitutes a joint for relatively rotating the first and second bending pieces 51, 52 in the right and left directions. The second rotation shaft 62 constitutes a joint for relatively rotating the second and third bending pieces 52, 53 in the up and down directions. The third rotation shaft 63 constitutes a joint for relatively rotating the third and fourth bending pieces 53, 54 in the right and left directions. Further, the fourth rotation shaft 64 constitutes a joint for relatively rotating the fourth and fifth bending pieces 54, 55 in the up and down direction.

In the embodiment, axial directions of the first, second, third, and fourth rotation shafts 61, 62, 63, 64 are alternately offset by 90°. That is, the bending pieces 51, 52 and the bending pieces 53, 54 are rotated in the right and left direction. The bending pieces 52, 53 and the bending pieces 54, 55 are rotated in the up and down direction. Further, axial directions of the rotation shafts 61, 62, 63, 64 are orthogonal to the center axis (long axis) L of the bending portion 46 (refer to FIGS. 17, 18A, and 18B). The center axis L agrees with the long axis of the insertion portion 42.

As shown in FIGS. 18A and 18B, the bending pieces 51, 52, 53, 54, 55 have tongue-piece-shaped coupling portions 65 projecting from the end edges thereof. When the coupling portions 65 are overlapped with each other, the rotation shafts 61, 62, 63, 64 pass through the overlapping portions. That is, the rotation shafts 61, 62, 63, 64 are rivet-like shaft members.

The multijointed bending mechanism arranged as described above is covered with a flexible casing (not shown). The bending portion 46 is constructed by this configuration.

A first set of a pair of the non-expandable manipulation wires 56 (56a, 56b) connected to the first bending piece 51, a second set of a pair of the non-expandable manipulation wires 57 (57a, 57b) connected to the second bending piece 52, a third set of a pair of the non-expandable manipulation wires 58 (58a, 58b) connected to the third bending piece 53, and a fourth set of a pair of the non-expandable manipulation wires 59 (59a, 59b) connected to the fourth bending piece 51 are inserted into the insertion portion 42.

As shown in FIG. 18A, the manipulation wires 56a, 56b are laterally symmetrically disposed in the bending portion 46 with respect to the center axis L. The distal ends of the manipulation wires 56a, 56b extend to the region in the first bending piece 51 and are connected to the first bending piece 51.

The direction of the center axis of the first bending piece 51 approximately agrees with the direction of the center axis L. On one plane which passes through both the direction of the center axis of the first bending piece 51 and the axial direction of the first rotation shaft 61, the right half portion of the first bending piece 51 is called a right portion, and the left half portion of the first bending piece 51 is called a left portion.

The distal end of the manipulation wire 56a described above is connected to the right portion of the first bending piece 51. Further, the distal end of the manipulation wire 56b is connected to the left portion of the first bending piece 51. When the manipulation wire 56a is pulled to the base end (proximal end) side shown in FIG. 18A, the first bending piece 51 is rotated rightward around the first rotation shaft 61. Further, when the manipulation wire 56b is pulled to the proximal end side, the first bending piece 51 is rotated leftward around the first rotation shaft 61. As described above, the manipulation wires 56 rotate the first bending piece 51.

As shown in FIG. 18B, the manipulation wires 57a, 57b are vertically symmetrically disposed in the bending portion 46 with respect to the center axis L. The distal ends of the manipulation wires 57a, 57b extend to the region in the second bending piece 52 and are connected to the second bending piece 52.

The direction of the center axis of the second bending piece 52 approximately agrees with the direction of the center axis L. On one plane which passes through both the direction of the center axis of the second bending piece 52 and the axial direction of the second rotation shaft 62, the upper half portion of the second bending piece 52 is called an upper portion, and the lower half portion of the second bending piece 52 is called a lower portion.

The distal end of the manipulation wire 57a described above is connected to the upper portion of the second bending piece 52. Further, the distal end of the manipulation wire 57b is connected to the lower portion of the second bending piece 52. When the manipulation wire 57a is pulled to the base end (proximal end) side shown in FIG. 18B, the second bending piece 52 is rotated upward around the second rotation shaft 62. Further, when the manipulation wire 57b is pulled to the proximal end side shown in FIG. 18B, the second bending piece 52 is rotated downward around the second rotation shaft 62. As described above, the manipulation wires 57 rotate the second bending piece 52.

As shown in FIG. 18A, the manipulation wires 58a, 58b are laterally symmetrically disposed in the bending portion 46 with respect to the center axis L. The distal ends of the manipulation wires 58a, 58b extend in the region of the third bending piece 53 and are connected to the third bending piece 53.

The direction of the center axis of the third bending piece 53 approximately agrees with the direction of the center axis L. On one plane which passes through both the direction of the center axis of the third bending piece 53 and the axial direction of the third rotation shaft 63, the right half portion of the third bending piece 53 is called a right portion, and the left half portion of the third bending piece 53 is called a left portion.

The distal end of the manipulation wire 58a described above is connected to the right portion of the third bending piece 53. Further, the distal end of the manipulation wire 58b is connected to the left portion of the third bending piece 53. When the manipulation wire 58a is pulled to the base end (proximal end) side shown in FIG. 18A, the third bending piece 53 is rotated rightward around the third rotation shaft 63. Further, when the manipulation wire 58b is pulled to the proximal end side shown in FIG. 18A, the third bending piece 53 is rotated leftward around the third rotation shaft 63. In this manner, the manipulation wires 58 rotate the third bending piece 53.

As shown in FIG. 18B, the manipulation wires 59a, 59b are vertically symmetrically disposed in the bending portion 46 across the center axis L. Distal ends of the manipulation wires 59a, 59b extend into a region in the fourth bending piece 54 and connected to the fourth bending piece 54.

A direction of the center axis of the fourth bending piece 54 approximately agrees with the direction of the center axis L. On one plane which passes through both the center axis direction of the fourth bending piece 54 and the axial direction of the fourth rotation shaft 64, an upper half portion of the fourth bending piece 54 is called an upper portion, and a lower half portion of the fourth bending piece 54 is called a lower portion.

A distal end of the manipulation wire 59a described above is connected to the upper portion of the fourth bending piece 54. Further, a distal end of the manipulation wire 59b is connected to the lower portion of the fourth bending piece 54. When the manipulation wire 59a is pulled to the base end (proximal end) side shown in FIG. 18B, the fourth bending piece 54 is rotated upward around the fourth rotation shaft 64. When the manipulation wire 59b is pulled to the proximal end side shown in FIG. 18B, the fourth bending piece 54 is rotated downward around the fourth rotation shaft 64. As described above, the manipulation wires 59 rotate the fourth bending piece 54.

As described above, the pairs of manipulation wires 56, 57, 58, 59, which individually correspond to one another, are connected to the bending pieces 51, 52, 53, 54. When the pairs of the manipulation wires 56, 57, 58, 59 are appropriately selected and pushed and pulled in the bending portion 46, the bending pieces 51, 52, 53, 54 are independently rotated.

Various methods can be employed to connect the distal ends of the manipulation wires 56, 57, 58, 59 to the bending pieces 51, 52, 53, 54. The connection is made as described below in the embodiment.

As shown in FIG. 18A, in a proximal end portion of the first bending piece 51, cut and raised pieces 70, which project inward of the first bending piece 51, are formed in the right portion and the left portion of the first bending piece 51. The distal end of the manipulation wire 56*a* is inserted into the cut and raised piece 70 in the right portion, and fixed to the cut and raised piece 70 by brazing. Further, the distal end of the manipulation wire 56*b* is inserted into the cut and raised piece 70 in the left portion, and fixed to the cut and raised piece 70 by brazing.

Further, as shown in FIG. 18B, in the proximal end portion of the second bending piece 52, cut and raised pieces 70, which project inward of the second bending piece 52, are formed in the upper portion and the lower portion of the second bending piece 52. The distal end of the manipulation wire 57*a* is inserted into the cut and raised piece 70 in the upper portion and fixed to the cut and raised piece 70 by brazing. Further, the distal end of the manipulation wire 57*b* is inserted into the cut and raised piece 70 in the lower portion and fixed to the cut and raised piece 70 by brazing.

Further, as shown in FIG. 18A, in the peripheral end of the proximal end portion of the third bending piece 53, cut and raised pieces 80, which recess inward of the third bending piece 53, are formed in the right portion and the left portion of the third bending piece 53. The distal end of the manipulation wire 58*a* is inserted into the cut and raised piece 80 in the right portion and fixed to the cut and raised pieces 80 by brazing. Further, the distal end of the manipulation wire 58*b* is inserted into the cut and raised piece 80 in the left portion and fixed to the cut and raised pieces 80 by brazing.

Further, as shown in FIG. 18B, in the peripheral end of the proximal end portion of the fourth bending piece 54, cut and raised pieces 91, which recess inward of the fourth bending piece 54, are formed in the upper portion and the lower portion of the fourth bending piece 54. The distal end of the manipulation wire 59*a* is inserted into the cut and raised piece 91 in the upper portion and fixed to the cut and raised pieces 91 by brazing. Further, the distal end of the manipulation wire 59*b* is inserted into the cut and raised piece 91 in the lower portion and fixed to the cut and raised pieces 91 by brazing.

The manipulation wires 56 are inserted into a guide sheath 66, the manipulation wires 57 are inserted into a guide sheath 67, the manipulation wires 58 are inserted into a guide sheath 68, and the manipulation wires 59 are inserted into a guide sheath 69, and they are individually guided up to the manipulation unit 41. The guide sheaths 66, 67, 68, 69 have flexibility and are formed of a sheath-like elastic member having elasticity, for example, an intimately wound coil, a resin tube, and the like. The inner holes of the guide sheaths 66, 67, 68, 69 act as guide members for guiding traveling directions of the manipulation wires 56, 57, 58, 59.

The distal end of each guide sheath is connected not to a bending piece to which the manipulation wire to be guided by the guide sheath itself is connected but to a bending piece disposed nearer to the proximal end side than the above bending piece. For example, the distal ends of guide sheaths 66*a*, 66*b* are connected to the second bending piece 52. The distal ends of guide sheaths 67*a*, 67*b* are connected to the third bending piece 53. Further, the distal ends of guide sheaths 68*a*, 68*b* are connected to the fourth bending piece 54.

Note that proximal ends of the guide sheaths may be connected to the proximal end portion of the bending portion 46 (the distal end of the flexible tube 45).

Next, how the manipulation wires and the guide sheaths are disposed in the bending pieces will be explained referring to FIGS. 18A, 18B, 19A, 19B, 19C, and 19D.

Figure 19A:
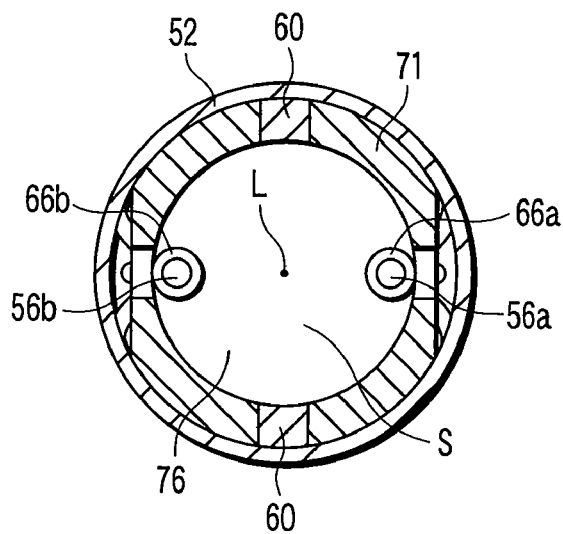
FIG. 19A is a lateral sectional view along a line A-A of FIG. 18B and shows a layout of manipulation wires and guide sheaths.

The distal ends of the guide sheaths 66*a*, 66*b* are fixed to a first wire guide 71 disposed in the second bending piece 52 and positioned to and supported by the second bending piece 52. The first wire guide 71 is formed of, for example, a ring-shaped sheet member as shown in FIGS. 18A, 18B, and 19A. The first wire guide 71 is fixed to an inner wall of the second bending piece 52 by pins 60 at both the vertical end edges thereof. As shown in FIG. 19A, cutouts are disposed in both the right and left ends of the first wire guide 71, respectively. An insertion hole 76, through which the contained members such as the guide sheaths 66*a*, 66*b* are inserted, is formed in a central portion of the first wire guide 71. The insertion hole 76 is formed in an approximately circular shape around the center axis L. The distal ends of the guide sheaths 66*a*, 66*b* are positioned and disposed in, for example, right/left inner wall portions in the insertion hole 76, respectively and fixed to the portions by brazing or the like. Accordingly, the distal ends of the guide sheaths 66*a*, 66*b* are disposed at the same distance from the center axis L. In other words, the distal ends of the guide sheaths 66*a*, 66*b* are disposed bilaterally symmetrically around the center axis L. With this configuration, the manipulation wires 56*a*, 56*b* passing through the guide sheaths 66*a*, 66*b* are also disposed bilaterally symmetrically around the center axis L. As described above, the first wire guide 71 plays a role as positioning/disposing mechanism for positioning and disposing the manipulation wire 56*a*, 56*b* and the guide sheaths 66*a*, 66*b*.

After the manipulation wires 56*a*, 56*b* project from the distal ends of the guide sheaths 66*a*, 66*b* as shown in FIG. 18A, they enter the first bending piece 51 while expanding, for example, right and left. The manipulation wire 56*a* is inserted into the cut and raised piece 70 in the right portion as described above. The manipulation wire 56*b* is inserted into the cut and raised piece 70 in the left portion as described above.

Note that although the distal ends of the guide sheaths 66*a*, 66*b* are directly fixed to the first wire guide 71, they may be indirectly fixed to the first wire guide 71 using a connector such as a connection ring (not shown).

Figure 19B:
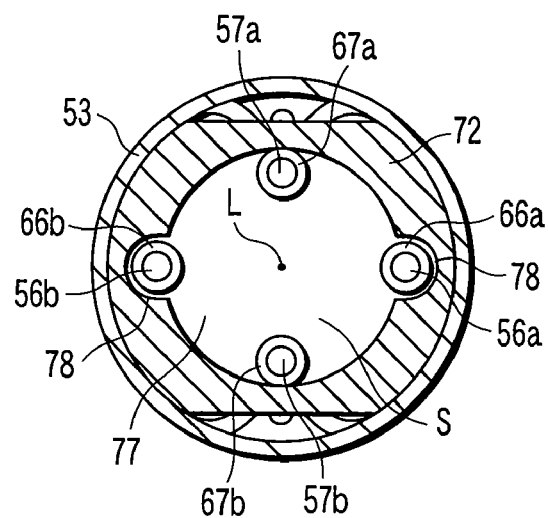
FIG. 19B is a lateral sectional view along a line B-B of FIG. 18B and shows a layout of manipulation wires and guide sheaths.

As shown in FIGS. 18A, 18B and 19B, the distal ends of the guide sheaths 67*a*, 67*b* are fixed to a second wire guide 72 disposed in the third bending piece 53 and positioned to and supported by the third bending piece 53. The second wire guide 72 is formed of, for example, a ring-like sheet-shaped member. The second wire guide 72 is fixed to the inner wall of the third bending piece 53 by pins 60 at both the end edges thereof. As shown in FIG. 19B, cut-outs are formed in the upper and lower end edges of the outer peripheral portion of the second wire guide 72. Guide sheaths 67*a*, 67*b* are brazed to the cut-outs. That is, the cut-outs are brazed portions.

An insertion hole 77, through which the contained members such as the guide sheaths 66*a*, 66*b* and the guide sheaths 67*a*, 67*b* are inserted, is formed at the center of the second wire guide 72. The insertion hole 77 is formed in a circular shape about the center axis L. The radius of the insertion hole 77 is smaller than that of the insertion hole 76. The distal ends of the guide sheaths 67*a*, 67*b* are positioned and disposed in, for example, the upper/lower inner wall portions in the insertion hole 77, respectively and fixed to the positions by brazing or the like. Accordingly, the distal ends of the guide sheaths 67*a*, 67*b* are disposed at the same distance from the center axis L. In other words, the distal ends of the guide sheaths 67*a*, 67*b* are vertically symmetrically disposed with respect to the center axis L. With this configuration, the manipulation wires 57a, 57b passing through the guide sheaths 67a, 67b are also vertically symmetrically disposed with respect to the center axis L. As described above, the second wire guide 72 plays a role as positioning/disposing mechanism for positioning and disposing the manipulation wires 57a, 57b and the guide sheaths 67a, 67b.

Further, as shown in FIG. 18B, groove portions 78 are formed in the right/left inner wall portions in the insertion hole 77. The guide sheath 66a is fitted into the groove portion 78 in the right inner wall portion so that it is free to advance and retreat. Further, the guide sheath 66b is fitted into the groove portion 78 in the left inner wall portion so that it is free to advance and retreat. With this configuration, the guide sheaths 66a, 66b are positioned and held by the second wire guide 72. At this time, the guide sheaths 67a, 67b are disposed inwards of the guide sheaths 66a, 66b (nearer to the center axis L) with respect to a direction vertical to the axial direction of the first rotation shaft 61 and the second rotation shaft 62 (in the direction of the center axis L). Accordingly, the manipulation wires 57a, 57b are disposed inwards of the manipulation wires 56a, 56b with respect to the direction of the center axis L. That is, in this case, the second wire guide 72 plays a role as positioning/disposing mechanism for executing positioning so that the guide sheaths 67a, 67b are disposed inwards of the guide sheaths 66a, 66b (the manipulation wires 57a, 57b are disposed inwards of the manipulation wires 56a, 56b).

After the manipulation wires 57a, 57b, which are guided by the guide sheaths 67a, 67b, project from the distal ends of the guide sheaths 67a, 67b as shown in FIG. 5B, they enter the second bending piece 52 while expanding, for example, up and down. The manipulation wire 57a is inserted into the cut and raised piece 70 in the upper portion as described above. The manipulation wire 57a is inserted into the cut and raised piece 70 in the lower portion as described above.

Note that although the distal ends of the guide sheaths 67a, 67b are directly fixed to the second wire guide 72, they may be indirectly fixed to the second wire guide 72 using a connector such as a connecting ring (not shown).

In the third bending piece 53, the guide sheaths 67a, 67b are disposed inwards of the guide sheaths 66a, 66b (nearer to the center axis L) as shown in FIG. 18B. Accordingly, a space S is formed around the periphery of the center axis L. Contained members, a surgical function unit to be assembled to the distal end portion 47 (for example, the grip forceps 48), and the like are disposed in the space S.

As shown in FIGS. 17, 18A and 18B, cut and raised pieces 79, which are recessed to the inside of the fourth bending piece 54, are formed in the right inner wall portion and the left inner wall portion in the end edge portion of the distal end of the fourth bending piece 54. The distal end of the guide sheath 68a is fixed to the cut and raised piece 79 in the right inner wall portion by brazing or the like. The distal end of the guide sheath 68b is fixed to the cut and raised piece 79 in the left inner wall portion by brazing or the like.

Note that the distal ends of the guide sheaths 68a, 68b may be fixed to the fourth bending piece 54 by connection rings (not shown).

As shown in FIG. 18A, after the manipulation wires 58a, 58b project from the distal ends of the guide sheaths 68a, 68b, they enter the third bending piece 53. As described above, the manipulation wire 58a is inserted into the cut and raised piece 80 in the right side portion. Further, the manipulation wire 58b is inserted into the cut and raised piece 80 in the left side portion as described above.

Note that the distal ends of the manipulation wires 58a, 58b may be fixed to the third bending piece 53 by connection rings (not shown).

Figure 19C:
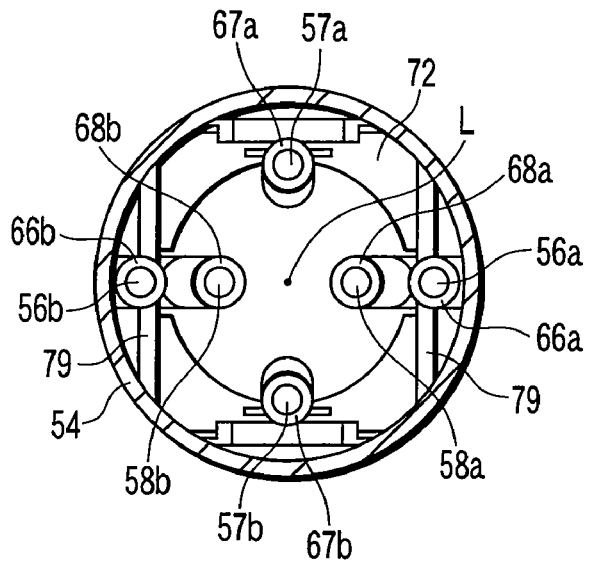
FIG. 19C is a lateral sectional view along a line C-C of FIG. 18B and shows a layout of manipulation wires and guide sheaths.

As shown in FIGS. 17, 18A and 19C, in the cut and raised pieces 80 and 79, the guide sheaths 66a, 66b are disposed more away externally from the center axis L than the cut and raised pieces 80, 79. To explain in detail, as shown in FIGS. 4 and 5A, the cut and raised pieces 80 have cut-out gaps 80a formed thereon, through which the guide sheaths 66a, 66b can be inserted. Further, the cut and raised pieces 79 have cut-out gaps 79a formed thereon, through which the guide sheaths 66a, 66b can be inserted. As shown in FIG. 17, the guide sheaths 66a, 66b pass through the cut-out gaps 80a from the inside of the third bending piece 53 and exit to the outside of the third bending piece 53. Further, the guide sheaths 66a, 66b reach the cut and raised pieces 79, pass through the cut-out gaps 79a, and enter the fourth bending piece 54.

Accordingly, as shown in FIG. 19C, the guide sheaths 68a, 68b are disposed inwards of the guide sheaths 66a, 66b (nearer to the center axis L) in a direction vertical to the axial direction of the first rotation shaft 61, the second rotation shaft 62, and the third rotation shaft 63 (in the direction of the center axis L). Therefore, the manipulation wires 58a, 58b are disposed inwards of the manipulation wires 56a, 56b in the direction of the center axis L. Thus, the cut and raised pieces 79, 80 play a role as positioning/disposing mechanism for executing positioning of the manipulation wires 58a, 58b and the guide sheaths 68a, 68b.

Further, as shown in FIG. 19C, the guide sheaths 68a, 68b are disposed inwards of the guide sheaths 66a, 66b and the guide sheaths 67a, 67b (nearer to the center axis L) in a direction vertical to the axial direction of the first rotation shaft 61, the second rotation shaft 62, and the third rotation shaft 63 (in the direction of the center axis L). Accordingly, the manipulation wires 58a, 58b are disposed inwards of the manipulation wires 56a, 56b and the manipulation wires 57a, 57b.

As shown in FIGS. 17 and 18B, cut and raised pieces 90, which are recessed to the inside of the fifth bending piece 55, are formed in the upper inner wall portion and the lower inner wall portion of the fifth bending piece 55 in the end edge portion of the fifth bending piece 55 on the distal end side thereof. The distal end of the guide sheath 69b is fixed to the cut and raised piece 90 in the upper inner wall portion by brazing or the like. The distal end of the guide sheath 69b is fixed to the cut and raised piece 90 in the lower inner wall portion by brazing or the like.

Note that the distal ends of the guide sheaths 69a, 69b may be fixed to the fifth bending piece 55 by connection rings (not shown).

As shown in FIG. 18B, after the manipulation wires 59a, 59b project from the distal ends of the guide sheaths 69a, 69b, they enter the fourth bending piece 54. As described above, the manipulation wire 59a is inserted into the cut and raised piece 91 in the upper side portion. Further, the manipulation wire 59b is inserted into the cut and raised piece 91 in the lower side portion as described above.

As shown in FIG. 17, in the cut and raised pieces 91 and the cut and raised pieces 90, the guide sheaths 67a, 67b are disposed more away externally from the center axis L than the cut and raised pieces 91, 90. To explain in detail, as shown in FIG. 17, the cut and raised pieces 91 have cut-out gaps 91a formed thereon, through which the guide sheaths 67a, 67b can be inserted. Further, the cut and raised pieces 90 have cut-out gaps 90a formed thereon, through which the guide sheaths 67a, 67b can be inserted. As shown in FIG. 17, the guide sheaths 67*a*, 67*b* pass through the cut-out gaps 91*a* from the inside of the fourth bending piece 54 and exit to the outside of the fourth bending piece 54. Further, the guide sheaths 67*a*, 67*b* reach the cut and raised pieces 90, pass through the cut-out gaps 90*a*, and enter the fifth bending piece 55.

Figure 19D:
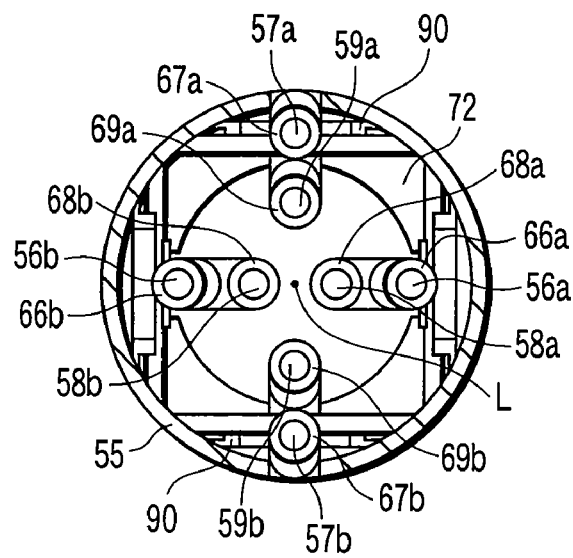
FIG. 19D is a lateral sectional view along a line D-D of FIG. 18B and shows a layout of manipulation wires and guide sheaths.

Accordingly, as shown in FIG. 19D, the guide sheaths 69*a*, 69*b* are disposed inwards of the guide sheaths 67*a*, 67*b* in a direction vertical to the axial direction of the first rotation shaft 61, the second rotation shaft 62, the third rotation shaft 63 and the fourth rotation shaft 64 (in the direction of the center axis L). Accordingly, the manipulation wires 59*a*, 59*b* are disposed inwards of the manipulation wires 57*a*, 57*b* in the direction of the center axis L. Thus, the cut and raised pieces 91, 90 play a role as positioning/disposing mechanism for executing positioning of the manipulation wires 59*a*, 59*b* and the guide sheaths 69*a*, 69*b*.

As described above, the wire guides and the cut and raised pieces play the role as the positioning/disposing mechanism for specifying the positions of the guide sheaths and at the same time play the role as the positioning/disposing mechanism for determining the positions of the manipulation wires which are individually guided by the guide sheaths.

As shown in FIG. 17, the fifth bending piece 55 is a bending piece positioned at the most extreme proximal end of the bending portion 46. That is, it is possible to assume that the fifth bending piece 55 is the proximal end portion of the bending portion 46. A connector member 94 such as a connection ring is disposed in the distal end of the flexible tube 45. The fifth bending piece 55 is coupled with the connector member 94. Further, the fifth bending piece 55 may be rotatably coupled with the connector member 94. In this mode, it is also possible to assume that the connector member 94 is the proximal end portion of the bending portion 46.

Further, the contained members such as a manipulation wire 93 and an electric wire are disposed in the space of the bending pieces in which the manipulation wires, the guide sheaths, and the positioning/disposing mechanism are not disposed. Further, the guide sheath and the manipulation wire on the proximal end side are disposed inwards of the guide sheath and the manipulation wire on the distal end side. Accordingly, the space S is formed in a central region (in the periphery of the center axis L) of the bending piece on the distal end side. In particular, the large space S is formed from the first bending piece 51 to the third bending piece 53. Thus, the contained members, the surgical function portion to be assembled to the distal end portion 47 (for example, the grip forceps 48), and the like are disposed in the space S. Further, function parts such as an actuator and a sensor may be disposed in the space S.

As shown in FIG. 16, the manipulation unit 41 is provided with a bending portion manipulation mechanism and an end effector manipulation mechanism. The bending portion manipulation mechanism is provided with drive motors 95, 96, 97, 98 for pushing and pulling the manipulation wires 56, 57, 58, 59, respectively. Further, the end effector manipulation mechanism is provided with a drive motor 100 for pushing and pulling the manipulation wire 92. The manipulation wires 56, 57, 58, 59 correspond to the bending pieces (targets to be rotated) 51, 52, 53, 54 and execute rotating manipulations. The manipulation wire 92 manipulates the grip forceps 48.

Pulleys 99 are attached to drive shafts of the drive motors 95, 96, 97, 98, 100, respectively. The respective drive shafts may be coupled with the respective pulleys 99 through reducers (not shown). The manipulation wires 56, 57, 58, 59, 92 are trained round the respective pulleys 99. The drive motors 95, 96, 97, 98, 100 are individually driven, respectively, and when the pulleys 99 are rotated, the manipulation wires 56, 57, 58, 59, 92 trained around the pulleys 99 are pushed and pulled.

Although the bending portion manipulation mechanism and the end effector manipulation mechanism use transmission mechanisms making use of the pulleys 99, they may use, for example, a gear mechanism and the like making use of a pinion gear and a rack. Further, the bending portion manipulation mechanism and the end effector manipulation mechanism may use other types of drive actuators in place of the drive motors 95, 96, 97, 98, 100.

As shown in FIG. 16, the manipulation unit 41 is connected to the surgical instrument controller 37 through a cable 201. The bending manipulation unit 39 as the manipulation input unit is connected to the surgical instrument controller 37 through a cable 204. In FIG. 16, the surgical instrument controller 37 is provided with a power supply cord 205.

The bending manipulation unit 39 includes a joystick (manipulation input unit) 203 for instructing a position and an attitude of the surgical instrument 40. The joystick 203 includes four joystick switches 203*a*, 203*b*, 203*c*, 203*d* continuously connected in four stages. The joystick switches 203*a*, 203*b*, 203*c*, 203*d* are attached to a manipulation box 210.

When the joystick switches 203*a*, 203*b*, 203*c*, 203*d* are selectively manipulated, the drive motors 95, 96, 97, 98 are individually driven corresponding to the manipulation. With this manipulation, the bending pieces 51, 52, 53, 54 are individually and independently driven in up, down, right, and left directions to thereby bend respective joint portions.

The surgical instrument distal end movement controller 18 can move the distal end portion 47 to a desired position by the movement according to the manipulation of the joystick 203. That is, the surgical instrument distal end movement controller 18 constitutes the surgical instrument 40 which is arranged as a master/slave type and driven electrically. Note that, when the joystick 203 is manipulated by an operator and the like after a control for moving the surgical instrument 40 is set, preference is given to an instruction for manipulating the joystick 203.

As shown in FIG. 1, the surgical instrument controller 37 is provided with a function control input portion 121 for inputting an instruction output from the joystick 203, a condition for controlling the function of the joystick 203, and the like, a motor driver (surgical instrument drive controller) 122 for controlling the drive of the drive motors 95, 96, 97, 98, and a motor unit communication unit 123 connected to the surgical instrument drive unit 38 through the cable 201 for executing communication with the surgical instrument drive unit 38.

The surgical instrument controller 37 transmits a control signal for driving the drive motors 95, 96, 97, 98 in response to the manipulation of the joystick 203 executed by the operator to the motor driver 122 and rotates the drive motors 95, 96, 97, 98. Encoders (not shown) are mounted on the drive motors 95, 96, 97, 98 to measure the numbers of revolution thereof. The encoders feedback-control the drive motors 95, 96, 97, 98 by generating signals according to the number of revolutions and transmitting the signals to the motor driver 122.

The relation between a multijointed structure in the bending portion 46 and the joystick 203 will be explained referring to FIGS. 20A, 20B and 21.

As shown in FIG. 20A, in a state that all the joint portions in the bending portion 46 project from the distal end portion 33, the joints disposed from the manipulation unit side (proximal end side) to the distal end side are sequentially referred to as J1, J2, J3, J4. A coordinate system is set using the joint J1 disposed nearest to the manipulation unit side as a reference.

In the coordinate system, a Y-axis direction agrees with a vertical direction of the image pickup device. It is assumed that the joints J1, J3 are bent about an X-axis, and the joints J2, J4 are bent about a Y-axis.

As shown in FIG. 21, the joystick 203 (manipulation input unit) includes joints J1', J2', J3', J4' which have the same structures as those of the joint J1 and the joints J2, J3, J4 located nearer to the distal end side than the joint J1.

The number of the joints and the bending directions of the joystick 203 are the same as those of the bending portion 46. The lengths of respective rods of the joystick 203 are set to values multiplied by an appropriate coefficient k so that the operator can easily manipulate them. When, for example, k=10 and the length of each rod of the surgical instrument 40 is 3 mm, the length of each rod of the joystick 203 (manipulation input unit) is set to 30 mm. Encoders (not shown) are assembled to the joints J1', J2', J3', J4' to measure bent angles. The information of the bent angles measured by the encoders is sent to the surgical instrument controller 37. The surgical instrument controller 37 generates drive signals corresponding to the angle information (the joints J1', J2', J3', J4') and bends the joints J1, J2, J3, J4 by rotating the drive motors 95, 96, 97, 98, respectively. When the joints J1', J2', J3', J4' are bent as shown in, for example, FIG. 21, the joints J1, J2, J3, J4 are bent as shown in FIG. 20B.

Since the bending portion 46 has the plurality of joints, the distal end of the surgical instrument 40 can be moved to an arbitrary position and an arbitrary attitude so that an affected area can be more easily cut out and exfoliated than ever before. Further, since the joint structure of the surgical instrument 40 is caused to equally correspond to that of the manipulation input unit, the operator can easily operate the surgical instrument having the plurality of joints.

Further, the drive motor 100 also has a motor driver, a motor unit communication unit, and the like similarly to the drive motors 95, 96, 97, 98. The grip forceps 48 is manipulated by manipulating a manipulation body such as a handle (function control/input unit) 125 disposed in the manipulation unit 41 and the like.

Note that the manipulation input unit may be preferably provided with a first manipulation switch corresponding to the first bending piece 51, a second manipulation switch corresponding to the second bending piece 52, a third manipulation switch corresponding to the third bending piece 53, and a fourth manipulation switch corresponding to the fourth bending piece 54. When, for example, the first manipulation switch is depressed, the first bending piece 51 is bent. Further, the manipulation unit 41 may be preferably provided with a switch device (manipulation switch) for the bending manipulation. The manipulation input unit may use a pen type input unit for inputting a three-dimensional position.

Next, an operation when the surgical instrument 40 is used will be explained.

First, the insertion portion 21 is inserted in a body cavity, and the insertion portion 42 is inserted from the insertion port 28 into the insertion channel in this state. The distal end portion 47 and the bending portion 46 project from the channel port 36 into the body cavity. Then, a work for gripping an affected area and the like in the body cavity is executed using the grip forceps 48 while observing them by the endoscope 2.

In this case, the bending portion 46 can be bent to an appropriate multijointed bent shape according to a state in the body cavity and a surgical procedure. That is, when the joystick 203 is manipulated and the bending pieces 51, 52, 53, 54 are individually rotated, the bending portion 46 is bend to an appropriate shape.

When, for example, the drive motor 95 is driven, the manipulation wires 56a, 56b trained around the pulley 99 in the drive motor 95 are pushed and pulled. With this operation, the first bending piece 51 is independently rotated. When the drive motor 96 is driven, the manipulation wires 57a, 57b trained around the pulley 99 in the drive motor 96 are pushed and pulled. With this operation, the second bending piece 52 is independently rotated. When the drive motor 97 is driven, the manipulation wires 58a, 58b trained around the pulley 99 in the drive motor 97 are pushed and pulled. With this operation, the third bending piece 53 is independently rotated. Further, when the drive motor 98 is driven, the manipulation wires 59a, 59b trained around the pulley 99 in the drive motor 98 are pushed and pulled. With this operation, the fourth bending piece 54 is independently rotated.

Accordingly, the bending pieces 51, 52, 53, 54 are independently rotated by appropriately bending the joystick 203 so that the bending portion 46 is bent. The bending portion 46 is bend even to a complicated shape by adjusting the direction in which the joystick 203 is rotated and the amount of rotation thereof.

As described above, in the embodiment, since the manipulation wires are disposed in the respective bending pieces, it is possible to independently rotate only an arbitrary bending piece. Accordingly, in the embodiment, since the bending mechanism has a plurality of degrees of freedom, a work can be easily executed even in a narrow region such as a body cavity.

In more detail, in the embodiment, since the bending pieces 51, 52, 53, 54 can be independently rotated (bend), the bending portion 46 can be partially bent also in a different direction. Thus, in the embodiment, the bending portion 46 can be bend into an appropriate shape according to a state of use. As a result, since the degree of freedom of bending of the bending portion 46 is increased, it is possible in the embodiment to easily execute even a complicated work in a narrow body cavity region as compared with a case in which the bending portion 46 is uniformly bend. Further, in the embodiment, since the attitude of the bending portion 46 can be easily bent so that it does not disturb another surgical instrument or observation with the endoscope 2, the workability of the surgical instrument 40 can be increased.

Since the positions of the guide sheaths are determined in the bending portion 46, the embodiment can prevent the interference between the contained members including the guide sheaths. Further, the manipulation wires inserted into the guide sheaths are prevented from being in direct contact with the other manipulation wires or the contained members thanks to the guide sheaths. As a result, the embodiment can reduce the interference between the manipulation wires and the interference between the manipulation wires and the contained members.

Further, in the embodiment, the manipulation wire connected to the bending piece disposed in the proximal end side is disposed inwards of the manipulation wire connected to the bending piece disposed in the distal end side. Accordingly, the embodiment can easily secure the space inwards of the bending piece disposed in the distal end side. Thus, the embodiment can easily assemble, for example, the surgical function potion (for example, grip forceps 48) and the like to the space.

To explain in detail, the embodiment disposes the manipulation wire for rotating the bending piece disposed in the proximal end side and the guide sheath for guiding the manipulation wire inwards of the manipulation wire for rotating the bending piece disposed in the distal end side and the guide sheath for guiding the manipulation wire. With this configuration, the embodiment can easily secure the space S in the central region (inside) in the bending piece disposed in the distal end side. Accordingly, the embodiment can easily assemble, for example, surgical function parts and the like to the space S.

Since the embodiment compactly disposes the manipulation wire connected to the bending piece disposed in the proximal end side and the manipulation wire connected to the bending piece disposed in the distal end side, even if the number of the manipulation wires increases, the embodiment can prevent the manipulation wires from being entangled with each other. Further, since the embodiment can compactly dispose the plurality of the manipulation wires, it can reduce the diameter of the bending mechanism.

To explain in detail, in the embodiment, the manipulation wires 56, 57, 58, 59 can be disposed without being entangled with each other even though they pass through the narrow bending portion 46, and further the manipulation wires 56, 57, 58 can be disposed compactly. In other words, since the embodiment can prevent the manipulation wires 56, 57, 58 from being entangled with each other in the bending portion 46 and reduce occurrence of interference between the manipulation wires, it can smoothly execute a bending manipulation. Further, in the embodiment, since an allowance for disposing other contained member in the bending portion 46 can be made, the diameter of the bending portion 46 can be reduced.

Further, in the embodiment, a guide sheath, which guides a manipulation wire for rotating a bending piece, is connected to a bending piece located just behind the above bending piece (on the proximal end side). Thus, the embodiment can maximize the efficacy of the wire guide function achieved by the guide sheath. Further, the region in which the manipulation wires are separately exposed can be reduced. Accordingly, the embodiment can avoid any reduction in the wire guide functionality. Further, when, for example, the insertion portion 42 itself is twisted, the embodiment can alleviate the effect of the twist on the wire guide function of the guide sheaths.

Further, in the embodiment, the guide sheaths may be formed of an intimately wound metal coil. With this configuration, the embodiment can sufficiently withstand the abrupt rotating and bending actions of the bending pieces.

Next, another embodiment of the present invention will be explained referring to FIGS. 22 and 23. The overall configuration of an endoscope apparatus system in this embodiment is approximately the same as that of the above-described embodiment. However, a motor unit of a surgical instrument 40 is additionally provided with a mechanism 131 for rotating a bending portion 46 around the axis of an insertion portion 42 and a mechanism 132 for advancing the bending portion 46 in the axial direction of the insertion portion 42 in parallel therewith. Further, at least four joints are disposed in the bending portion 46. With this configuration, the position and the attitude of the distal end portion 47 are arbitrarily controlled. Further, a movement of the surgical instrument 40 corresponds to that of a manipulation input unit 140. A joystick type manipulation input unit having an advancing, retreating, and rotating joint structure is used as the manipulation input unit 140.

A coordinate system is set as shown in FIG. 22. The coordinate system uses a proximal end portion 141 of the manipulation input unit 140 as a reference and corresponds to the surgical instrument 40. In the coordinate system, the joint J1 moves forward and rearward, the joint J2 rotates in an axial direction, the joints J3, J5 are bent about a Y-axis, and the joints J4, J6 are bent about an X-axis. The rotation angles of the joints J2 to J6 are shown by θ2 to θ6, respectively. The lengths of respective rods are shown by L1 to L5 and the length of a distal end rod is shown by L6. Thus, conversion matrices in the respective joints J1, J2, J3, J4, J5, J6 are shown by Expression 1 from the kinematics of the manipulator (surgical instrument 40).

[Expression 1]

$$\text{Joint } J1: T_0^1 = \begin{pmatrix} 1 & 0 & 0 & 0 \\ 0 & 1 & 0 & 0 \\ 0 & 0 & 1 & -L_1 \\ 0 & 0 & 0 & 1 \end{pmatrix}$$

$$\text{Joint } J2: T_1^2 = \begin{pmatrix} \cos\theta_2 & -\sin\theta_2 & 0 & 0 \\ \sin\theta_2 & \cos\theta_2 & 0 & 0 \\ 0 & 0 & 1 & -L_2 \\ 0 & 0 & 0 & 1 \end{pmatrix}$$

$$\text{Joint } J3: T_2^3 = \begin{pmatrix} \cos\theta_3 & 0 & \sin\theta_3 & -L_3\sin\theta_3 \\ 0 & 1 & 0 & 0 \\ -\sin\theta_3 & 0 & \cos\theta_3 & -L_3\cos\theta_3 \\ 0 & 0 & 0 & 1 \end{pmatrix}$$

$$\text{Joint } J4: T_3^4 = \begin{pmatrix} 1 & 0 & 0 & 0 \\ 0 & \cos\theta_4 & -\sin\theta_4 & L_4\sin\theta_4 \\ 0 & \sin\theta_4 & \cos\theta_4 & -L_4\cos\theta_4 \\ 0 & 0 & 0 & 1 \end{pmatrix}$$

$$\text{Joint } J5: T_4^5 = \begin{pmatrix} \cos\theta_5 & 0 & \sin\theta_5 & -L_5\sin\theta_5 \\ 0 & 1 & 0 & 0 \\ -\sin\theta_5 & 0 & \cos\theta_5 & -L_5\cos\theta_5 \\ 0 & 0 & 0 & 1 \end{pmatrix}$$

$$\text{Joint } J6: T_5^6 = \begin{pmatrix} 1 & 0 & 0 & 0 \\ 0 & \cos\theta_6 & -\sin\theta_6 & L_6\sin\theta_6 \\ 0 & \sin\theta_6 & \cos\theta_6 & -L_6\cos\theta_6 \\ 0 & 0 & 0 & 1 \end{pmatrix}$$

Accordingly, a homogeneous conversion matrix is shown by Expression 2.

[Expression 2]

$$T_0^6 = T_0^1 T_1^2 T_2^3 T_3^4 T_4^5 T_5^6$$

$$= \begin{pmatrix} r_{11} & r_{12} & r_{13} & t_x \\ r_{21} & r_{22} & r_{23} & t_y \\ r_{31} & r_{32} & r_{33} & t_z \\ 0 & 0 & 0 & 1 \end{pmatrix}$$

Since the coordinate system uses the proximal end portion 141 as the reference, the position (x, y, z) and the attitude (θx, θy, θz) of the distal end portion of the manipulation input unit 140 are determined by Expression 3.

[Expression 3]

$$\begin{pmatrix} x \\ y \\ z \end{pmatrix}^T = \begin{pmatrix} t_x \\ t_y \\ t_z \end{pmatrix}^T$$

$$\begin{pmatrix} \theta_x \\ \theta_y \\ \theta_z \end{pmatrix}^T = \begin{pmatrix} a\sin(r_{32}/\cos\theta_y) \\ a\sin(-r_{31}) \\ a\sin(r_{21}/\cos\theta_y) \end{pmatrix}^T$$

The configuration of the surgical instrument 40 is different from that of the manipulation input unit 140. Accordingly, to operate the surgical instrument 40 by operating the manipulation input unit 140, it is necessary to match the position and the attitude of the surgical instrument 40 with those of the manipulation input unit 140. For this purpose, the rotation angles and the amounts of parallel (forward and rearward) movement of the respective joints of the surgical instrument 40 must be determined.

As described above, the movement of the surgical instrument 40 corresponds to that of the manipulation input unit 140. Accordingly, the position and the attitude of the surgical instrument 40 are determined by those of the manipulation input unit 140. Assuming that the configuration of the surgical instrument 40 is known, the rotation angles and the amounts of parallel movement of the respective configurations of the surgical instrument 40 can be determined by inverse kinematics. Inverse kinematics is a method of estimating the specific values of the joints (angles and the like thereof) from the position/attitude information of the manipulator (surgical instrument 40) in a work space. The joint parameter $\Phi$ of the respective joints 1, 2, ..., n are shown by Expression 4.

$$\Phi = (\theta_1, \theta_2, \ldots, \theta_n)^T \qquad \text{[Expression 4]}$$

The position and the attitude of the manipulator are shown by Expression 5.

$$E_p = (x_{Ep}, y_{Ep}, z_{Ep}, \text{Roll}_{Ep}, \text{Yaw}_{Ep}, \text{Pitch}_{Ep})^T \qquad \text{[Expression 5]}$$

Thus, the relation thereof is shown by Expression 6.

$$E_p = A(\Phi) \qquad \text{[Expression 6]}$$

Here, the target P of the position and the attitude of the manipulator is shown by Expression 7.

$$P_p = (x_{Pp}, y_{Pp}, z_{Pp}, \text{Roll}_{Pp}, \text{Yaw}_{Pp}, \text{Pitch}_{Pp})^T \qquad \text{[Expression 7]}$$

To place the manipulator in a Pp state, $\Phi$ must be determined to satisfy Expression 8.

$$P_p = A(\Phi) \qquad \text{[Expression 8]}$$

However, since these expressions are non-linear, ordinarily, Jacobian matrix $J(\Phi)$ is determined by subjecting Ep to partial differentiation by the factor of $\Phi$ to determine $\Phi$.

$$J(\Phi) = \begin{pmatrix} \frac{dx_{ep}}{d\theta_1} & \frac{dx_{ep}}{d\theta_2} & \cdots & \frac{dx_{ep}}{d\theta_n} \\ \frac{dy_{ep}}{d\theta_1} & \frac{dy_{ep}}{d\theta_2} & \cdots & \frac{dy_{ep}}{d\theta_n} \\ \frac{dz_{ep}}{d\theta_1} & \frac{dz_{ep}}{d\theta_2} & \cdots & \frac{dz_{ep}}{d\theta_n} \\ \frac{d\text{Roll}_{ep}}{d\theta_1} & \frac{d\text{Roll}_{ep}}{d\theta_2} & \cdots & \frac{d\text{Roll}_{ep}}{d\theta_n} \\ \frac{d\text{Yaw}_{ep}}{d\theta_1} & \frac{d\text{Yaw}_{ep}}{d\theta_2} & \cdots & \frac{d\text{Yaw}_{ep}}{d\theta_n} \\ \frac{d\text{Pitch}_{ep}}{d\theta_1} & \frac{d\text{Pitch}_{ep}}{d\theta_2} & \cdots & \frac{d\text{Pitch}_{ep}}{d\theta_n} \end{pmatrix} \qquad \text{[Expression 9]}$$

Expression 11 is determined from Expression 10.

$$\dot{\Phi} = J(\Phi)^{-1} \dot{E}_p \qquad \text{[Expression 10]}$$

$$P_p = A(\Phi) \qquad \text{[Expression 11]}$$

Then, $\Phi$ that satisfies Expression 11 is determined by a convergence calculation.

As a result, according to the embodiment, even when the configuration of the manipulation input unit 140 is different from that of the surgical instrument 40, the distal end of the surgical instrument 40 can be moved to an arbitrary position and an arbitrary attitude from the position and the attitude of the manipulation input unit 140, and an affected area can be cut out and exfoliated more easily than ever before.

The present invention can be also applied to a bending portion of an endoscope. The present invention can be applied to, for example, the bending mechanism of the bending portion in the insertion portion of the endoscope according to the embodiment described above. Further, the surgical instrument as a target of the present invention also includes a treatment catheter.

Note that, in the explanation of the embodiment described above, the numerals of the bending pieces, the manipulation wires, the guide sheaths, and the wire guides are used to explain the embodiment and do not always agree with the numerals described in the claims. For example, there are cases where a first bending piece in the claim is the second bending piece in the embodiment, and a second bending piece in the claim is the third bending piece in the embodiment.

<Additional Statement>

According to the above explanation, there can be obtained multijointed medical equipments according to the following items or arbitrary combinations of the following items and the items according the claims.

1. An endoscope surgical instrument including:
    an endoscope to observe an affected area in a body cavity;
    a surgical instrument to perform surgery on the affected area by passing through an insertion portion of the endoscope;
    at least one bending mechanism disposed in a distal end of the surgical instrument;
    manipulation mechanism for moving the distal end of the surgical instrument in a direction intended by an operator;
    control mechanism for controlling movement of the distal end of the surgical instrument in response to manipulation of the manipulation mechanism; and
    mechanism for operating the bending mechanism of the surgical instrument in response to a control signal from the control mechanism.

2. The endoscope surgical instrument according to item 1, wherein the surgical instrument includes a soft insertion portion and an end effector (surgical portion) for cutting out and exfoliating an affected area of a living body.

3. The endoscope surgical instrument according to item 1, wherein power for operating the bending mechanism is assembled in the vicinity of the distal end of the surgical instrument.

4. The endoscope surgical instrument according to item 1, in which power for operating the bending mechanism is disposed in a portion other than the vicinity of the distal end of the surgical instrument and which includes transmission mechanism for transmitting the power to the bending mechanism.

5. The endoscope surgical instrument according to item 1, including mechanism for moving the distal end of the surgical instrument forward and rearward.

What is claimed is:

1. A surgical instrument comprising:
    an end effector configured to operate on an operating portion in a body cavity;
    an accommodation portion configured to accommodate the end effector; and
    an insulating holding member, configured to hold the end effector, is accommodated in the accommodation portion of the end effector, and is configured to advance and retreat along an axial direction of the accommodation portion;

an insertion portion having the end effector, the holding member, and the accommodation portion disposed in a distal end portion;

movement manipulation mechanism connected to the end effector for moving the end effector to a position at which the end effector is accommodated in the accommodation portion and to a position at which the end effector is exposed from the accommodation portion along an axial direction of the accommodation portion, and moving the holding member along the axial direction of the accommodation portion through the end effector; and a multijointed bending mechanism which is disposed in the distal end portion side of the insertion portion and moves the distal end portion by being bent, the multijointed bending mechanism having:

a first bending piece which is the distal end portion of the insertion portion;

a second bending piece connected to the first bending piece so as to be rotatable around a first rotation shaft, and arranged on a proximal end side of the multijointed bending mechanism with respect to the first bending piece;

a third bending piece connected to the second bending piece so as to be rotatable around a second rotation shaft, and arranged on a proximal end side of the multijointed bending mechanism with respect to the second bending piece;

at least two first wires connected to the first bending piece and configured to rotate the first bending piece; and at least two second wires connected to the second bending piece and configured to rotate the second bending piece;

wherein the accommodation portion is formed in the first bending piece, and wherein a length from a proximal end portion of the holding member to a distal end portion of the end effector is $L1$, a length of the accommodation portion is $L2$, and a maximum amount of moving stroke of the holding member is $L3$, with $L1<L2$ and $L3>L1$.

2. The surgical instrument according to claim 1, wherein the end effector is a high frequency treatment electrode.

3. The surgical instrument according to claim 2, further comprising a mount/dismount portion which detachably mounts the end effector.

* * * * *